(12) United States Patent
Ahmadi

(10) Patent No.: US 9,345,636 B2
(45) Date of Patent: May 24, 2016

(54) SYSTEM AND PROCESSES FOR AUTOMATING AND VERIFYING MEDICATION ORDER FULFILLMENT COMPLIANCE AND MEDICATION ADMINISTRATION COMPLIANCE

(71) Applicant: Ahmad H. Ahmadi, Sugar Land, TX (US)

(72) Inventor: Ahmad H. Ahmadi, Sugar Land, TX (US)

(73) Assignee: DEA HEALTH SOLUTIONS, LLC, Sugar Land, TX (US)

( * ) Notice: Subject to any disclaimer, the term of this patent is extended or adjusted under 35 U.S.C. 154(b) by 158 days.

(21) Appl. No.: 14/165,142

(22) Filed: Jan. 27, 2014

(65) Prior Publication Data

US 2014/0214438 A1 Jul. 31, 2014

Related U.S. Application Data

(60) Provisional application No. 61/759,185, filed on Jan. 31, 2013.

(51) Int. Cl.
*A61J 1/03* (2006.01)
*G06F 19/00* (2011.01)
*A61J 7/00* (2006.01)

(52) U.S. Cl.
CPC .............. *A61J 1/035* (2013.01); *A61J 7/0084* (2013.01); *G06F 19/3462* (2013.01); *A61J 2200/30* (2013.01); *A61J 2205/10* (2013.01)

(58) Field of Classification Search
USPC .............................................. 206/459.5, 534
See application file for complete search history.

(56) References Cited

U.S. PATENT DOCUMENTS

| | | | | | |
|---|---|---|---|---|---|
| 5,788,079 | A | * | 8/1998 | Bouthiette | A61J 7/0069 206/534 |
| 2009/0277815 | A1 | * | 11/2009 | Kohl | A61J 1/035 206/531 |
| 2010/0000899 | A1 | * | 1/2010 | Burg | B65D 83/0463 206/459.1 |
| 2013/0319902 | A1 | * | 12/2013 | Tufi | A61J 1/035 206/534 |
| 2015/0209227 | A1 | * | 7/2015 | Bamberger | A61J 1/035 206/531 |
| 2015/0352009 | A1 | * | 12/2015 | Miller | A61J 1/035 206/534 |

* cited by examiner

*Primary Examiner* — Jacob K Ackun

(57) ABSTRACT

A system and processes for automating and verifying medication order fulfillment and medication administration compliance. A medication package is formed from a package back pane and blister housing, and filled in accordance to a prescription order. The package back pane has a medication housing color pattern that contrasts medication colorings of a prescribed medication, such that a number of empty medication blisters can be determined from a package image matrix generated by analyzing the medication housing color pattern, the medication colorings, and a plurality of reference marks on the package back pane from a captured image of the medication package. The package image matrix is compared to a previous package image matrix in order to determine if the prescribed medication has been administered properly. A unique prescription code of the medication package can program a processor with a scheduling profile, medication order information, and the package image matrix.

4 Claims, 24 Drawing Sheets

| Provided medication order information 33 and an order fulfillment processor 60, wherein the medication order information 33 details a prescribed medication 30 for a patient    201 |
|---|
| Retrieve a bulk package of the prescribed medication 30 and scan the national drug code into the order fulfillment processor 60    202 |
| Retrieve the package back pane 11 and blister housing 17 for a medication package 10 as dictated by the order fulfillment processor 60    210 |
| Scan the back pane code 22 in order to verify the package back pane 11 on the order fulfillment processor 60    211 |
| Position the medication order information 33 and a unique prescription code 21 on the package back pane 11    212 |
| Fill each of the plurality of medication blisters 18 with the prescribed medication 30 according to the medication placement display 23    222 |
| Seal the package back pane 11 to the blister housing 17    223 |
| Scan the medication package 10 with the digital imaging device 73 in order to send a scanned image 24 to the order fulfillment processor 60, wherein the medication package 10 displays the medication order information 33 and a unique prescription code 21    224 |

FIG. 11

SYSTEM AND PROCESSES FOR AUTOMATING AND VERIFYING MEDICATION ORDER FULFILLMENT COMPLIANCE AND MEDICATION ADMINISTRATION COMPLIANCE

The current application claims a priority to the U.S. Provisional Patent application Ser. No. 61/759,185 filed on Jan. 31, 2013.

FIELD OF THE INVENTION

The present invention relates generally to a system and method for packaging and administering pharmaceuticals. Additionally, the present invention is related to the fields of medication order fulfillment verification and record keeping, and medication administration compliance and record keeping. Furthermore, the present invention relates to automated computer-based labeling and image scan processing systems to label the medication with a unique prescription code that is used in methods for verifying and recording compliance in medication order fulfillment, administration, and record keeping

BACKGROUND OF THE INVENTION

Advances in health care have helped to dramatically increase the lifespan of patients and their quality of life through the development of more effective treatments, medication, and medical technologies. However, one of the leading causes of medical patient readmission and patient fatalities is accidental patient or caregiver non-compliance with medication administration. Many patients often forget to take their medication, take too many doses of their medication, take their medication in an incorrect interval, or take the wrong medication. Additionally, patients do not keep a log of their medication intake. Incorrect administration of medication in prescribed method can lead to serious medical complications, higher medical costs, and death. Most patients do not even keep a good medication intake log to help provide assistance in medical diagnosis. Even when patients use calendars, a caregiver, their own memory or other methods to help remind them to take a particular medication on time, there is no easy and automated way for them to verify if they are taking the correct medication or dosage. There is no easy way for a health care provider to track if their patients are taking their medication in the manner that they were prescribed. There is no easy and automated way for healthcare providers to immediately modify or cancel medication orders or for pharmaceutical manufactures to recall a medication after patient or caregivers have possession of the medication. Also, there is no easy or automated way for healthcare providers to alert patients who have taken a recalled pharmaceutical of the potential danger to the patients' lives.

Therefore it is the object of the present invention to provide a system and method for correctly administering medications and creating detailed records of administered medications to the level of the national drug code, lot number, and expiration date of each dose of medication. The present invention utilizes unique medication packages with color coded medication package housings and a unique prescription code that can be utilized to retrieve and record medication information per dose, and automatically alert patients to how and when they should administer each dose of medication. Images of the medication package are taken before and after each administration of medication. Current images are compared to previous images to ensure that doses are not missing and are administered at the correct times. Medication data per individual dose, healthcare provider administration instructions, medication administration data per administered dose, and patient information are stored on a central processor where they can be accessed by third party information systems via a communication network.

BRIEF DESCRIPTION OF THE DRAWINGS

FIG. 11 is a flowchart of the steps taken by the operator in the manufacturing process.

DETAIL DESCRIPTIONS OF THE INVENTION

All illustrations of the drawings are for the purpose of describing selected versions of the present invention and are not intended to limit the scope of the present invention.

The present invention provides a system and processes for automating and verifying medication order fulfillment compliance and medication administration compliance. The present invention utilizes a medication package 10 throughout three processes: a manufacturing process, a scheduling process, and an administration process. The manufacturing process dictates the assembly of medication packages in accordance to the data retrieved from the prescription orders of various patients. After manufacture, the medication packages are distributed to their respective destinations. The scheduling process can then be initiated by patients or their caregivers in order to ensure that medications are administered at the proper time and in the correct dose. The administration process is then used to verify the medication packages in order to determine if any medication has been improperly administered. If a dose has been skipped or taken ahead of schedule the patient or caregiver is notified, such that they can take proper action.

Figure 1:
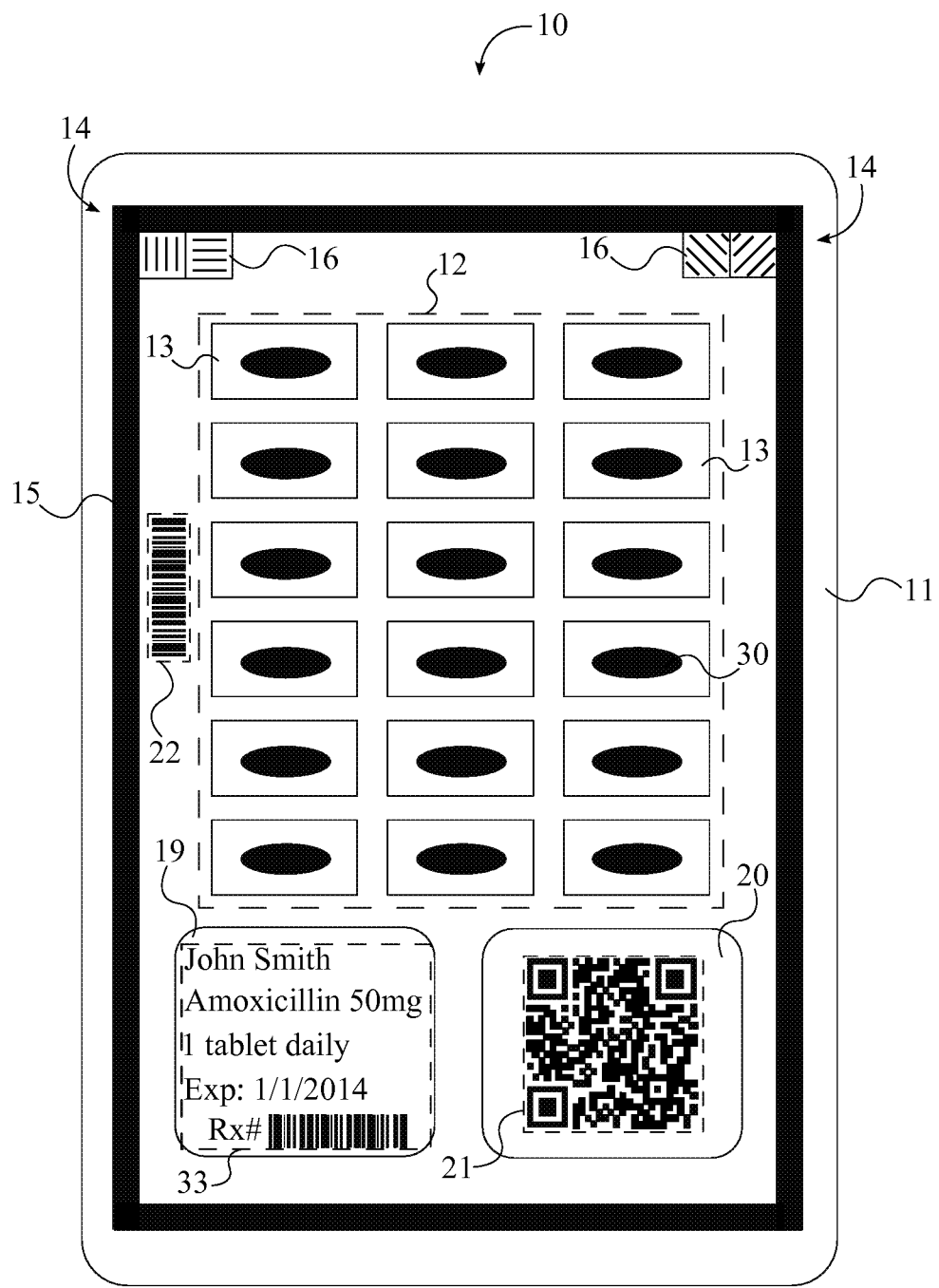
FIG. 1 is a front elevational view of the medication package filled with the prescribed medication.
Figure 2:
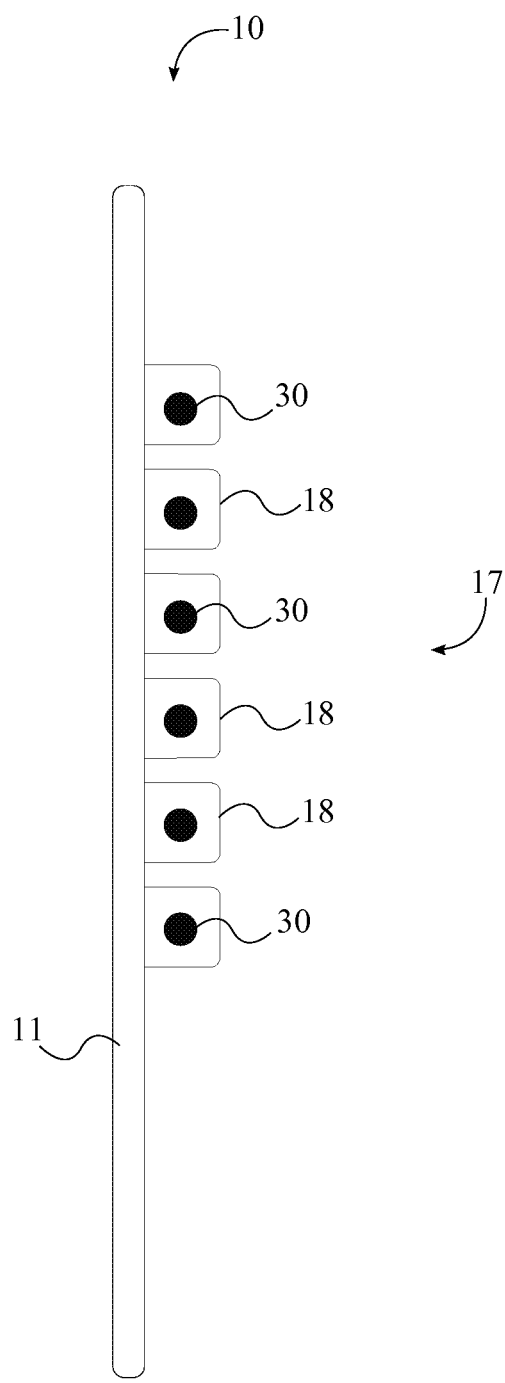
FIG. 2 is a left-side elevational view thereof.

In reference to FIG. 1 and FIG. 2, the medication package 10 contains a prescribed medication 30 in accordance with a prescription order, or prescription orders, for a patient. The medication package 10 comprises a package back pane 11, a medication housing color pattern 12, a plurality of reference marks 14, a blister housing 17, a back pane code 22, a first label 19 and a second label 20. The blister housing 17 comprises a plurality of medication blisters 18 for encapsulating the prescribed medication 30. The prescribed medication 30 may be one or more type of medication (e.g. amoxicillin; amoxicillin and oxybutynin; amoxicillin, oxybutynin, and lansoprazole). The package back pane 11 provides the body for which the back pane code 22, the medication housing color pattern 12, and the plurality of reference marks 14 are printed. The back pane code 22 is used to ensure that the package back pane 11 is correctly selected when the prescription order is filled. In the preferred embodiment of the present invention, the back pane code 22 is a barcode, however, any other type of code can be used, such as a quick response (QR) code. The medication housing color pattern 12 comprises a plurality of medication housing indicators 13; each of the plurality of medication housing indicators 13 indexing a single dose 32 or multiple doses of the prescribed medication (s) 30. The medication housing color pattern 12 can be printed using any number of colors and patterns, although colors are automatically selected that will contrast medication colorings 31 of the prescribed medication 30, thus causing the prescribed medication 30 to visibly stand out when placed against the medication housing color pattern 12.

In further reference to FIG. 1, the medication housing color pattern 12 and the plurality of reference marks 14 are positioned on the package back pane 11, with the plurality of reference marks 14 being positioned around the medication housing color pattern 12. The back pane code 22 is positioned on the package back pane 11 adjacent to the medication housing color pattern 12. The blister housing 17 is connected to the package back pane 11 in order to seal the prescribed medication 30 within the plurality of medication blisters 18 of the blister housing 17. The blister housing 17 is placed onto the package back pane 11, such that each of the plurality of medication blisters 18 of the blister housing 17 overlays one of the plurality of medication housing indicators 13. Additionally, the blister housing 17 is transparent, such that both the prescribed medication 30 and the medication housing color pattern 12 can be observed.

Further referencing FIG. 1, the first label 19 and the second label 20 are used to display information in regards to the patient and the prescribed medications 30 retained by the medication package 10. The first label 19 and the second label 20 can be used to directly display information, or information may be embedded and displayed in the form of a barcode, QR code, etc. Both the first label 19 and the second label 20 are positioned on the package back pane 11 adjacent to the medication housing color pattern 12. The first label 19 and the second label 20 can be printed directly onto the package back pane 11, or printed on a separate material, which is then adhered to the package back pane 11.

The first label 19 comprises medication order information 33, while the second label 20 comprises a unique prescription code 21. The medication order information 33 is derived from the prescription order and may contain data such as a national drug code (NDC) for the prescribed medication 30, the name of the patient, the strength of the prescribed medication 30, the number of doses per day, administration instructions, etc. The unique prescription code 21 also references or embeds information in regards to the patient and the administration information for the prescribed medication 30. Additionally, the unique prescription code 21 references or embeds the NDC, lot number, and expiration date for individual doses of the prescribed medication 30. Furthermore, the unique prescription code 21 references or embeds an image matrix for each of the plurality of medication blisters 18. When the unique prescription code 21 is scanned, the embedded information is directly retrieved from the unique prescription code 21 and any referenced information can be retrieved from the central processor 62. In the preferred embodiment of the present invention, the unique prescription code 21 is a QR code, however, any other type of code can be used, such as a barcode.

Each time a single dose 32 of the prescribed medication 30 is administered, a package image matrix of the plurality of medication blisters 18 is created using the medication housing color pattern 12 and the medication colorings 31 of the prescribed medication 30. The package image matrix is compared to a package image matrix created at the end of the manufacturing process in order to detect if the medication package 10 has been damaged or tampered with, or if any of the prescribed medication 30 is taken or missing. Two types of reference markings are used to ensure that the package image matrices can be properly compared. As such, the plurality of reference marks 14 comprises a perimeter mark 15 and a plurality of color code marks 16. The perimeter mark 15 is positioned around the medication housing color pattern 12 and provides straight edge references to ensure that scanned images of the medication package 10 are properly aligned in order to create the package image matrix. In the preferred embodiment of the present invention, four color code marks are used, however, any number can be used in other embodiments of the present invention. Similar to the perimeter mark 15, the plurality of color code marks 16 is positioned around the medication housing color pattern 12. The plurality of color code marks 16 is used to compensate for different levels of light when an image of a medication package 10 is taken. The medication housing color pattern 12 and the medication colorings 31 are referenced to the plurality of color code marks 16 when an image is taken. The plurality of color code marks 16 of the current image are then compared to an image of the plurality of color code marks 16 at the time of manufacture or from the last image taken. The plurality of medication blisters 18 can then be compared to a previous plurality of medication blisters 18 using the package image matrices.

Figure 3:
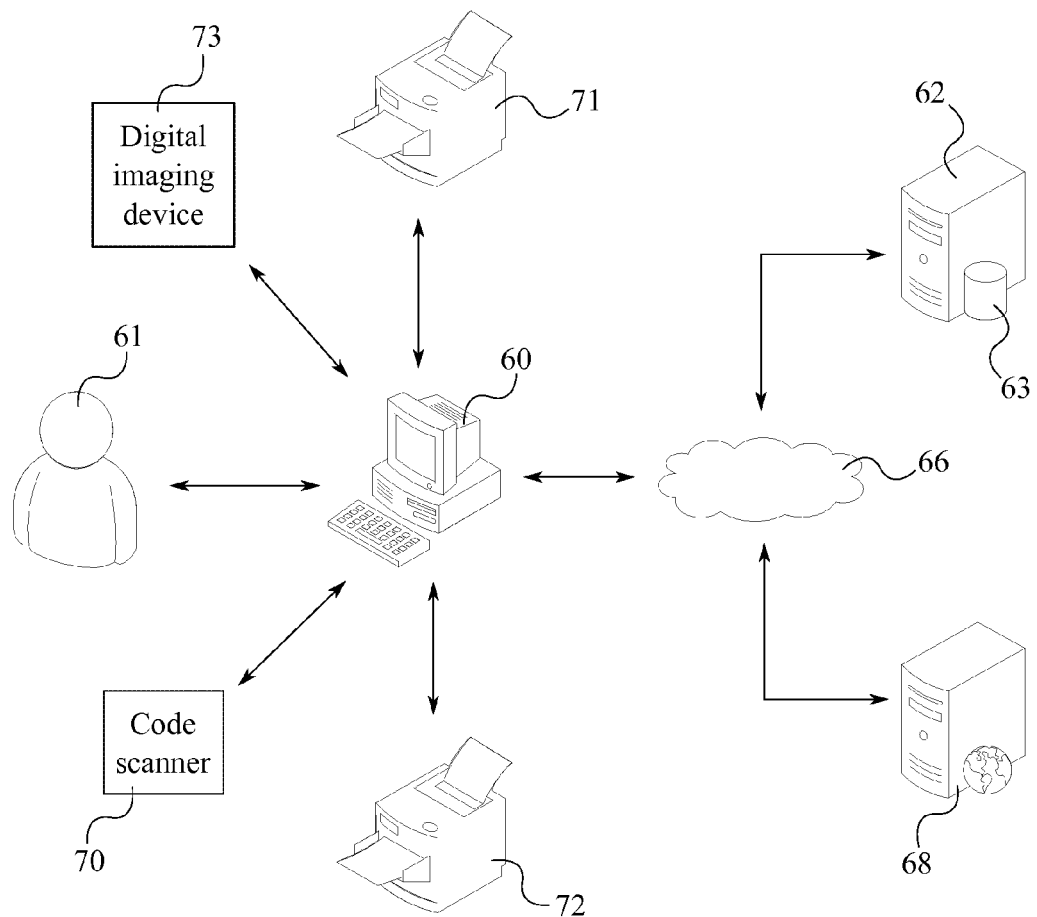
FIG. 3 is a diagram depicting the device and operator interactions for the manufacturing process.

In reference to FIG. 3, the manufacturing process for fulfilling medication orders utilizes an order fulfillment processor 60, a communication network 66, a central processor 62, third party information systems 68, a code scanner 70, and a digital imaging device 73. The manufacturing process may also include the use of a printer 71 or a package printer 72, depending on the desired method of assembling the medication package 10. The central processor 62, the third party information systems 68 and the order fulfillment processor 60 are connected to each other and are able to communicate with one another via the communication network 66. The communication network 66 can be any type of public or private network. The central processor 62 is used to store and manage data for multiple patients. Data stored on the central processor 62 can include but is not limited to the medication order information 33, a package image matrix, images of the medication package 10, administrative and manufacturing records, etc. Healthcare providers can utilize the third party information systems 68 to remotely transfer patient information in regards to medication order fulfillment (i.e. the prescription order for the patient) to either the central processor 62 or the order fulfillment processor 60. If the prescription order is sent to the central processor 62, then the prescription order is stored on the central processor 62 for future reference, such as prescription refills. The order fulfillment processor 60 can be any type of electronic device, including but not limited to, a personal digital assistant (PDA), a mobile phone, a tablet or a computer.

Figure 4:
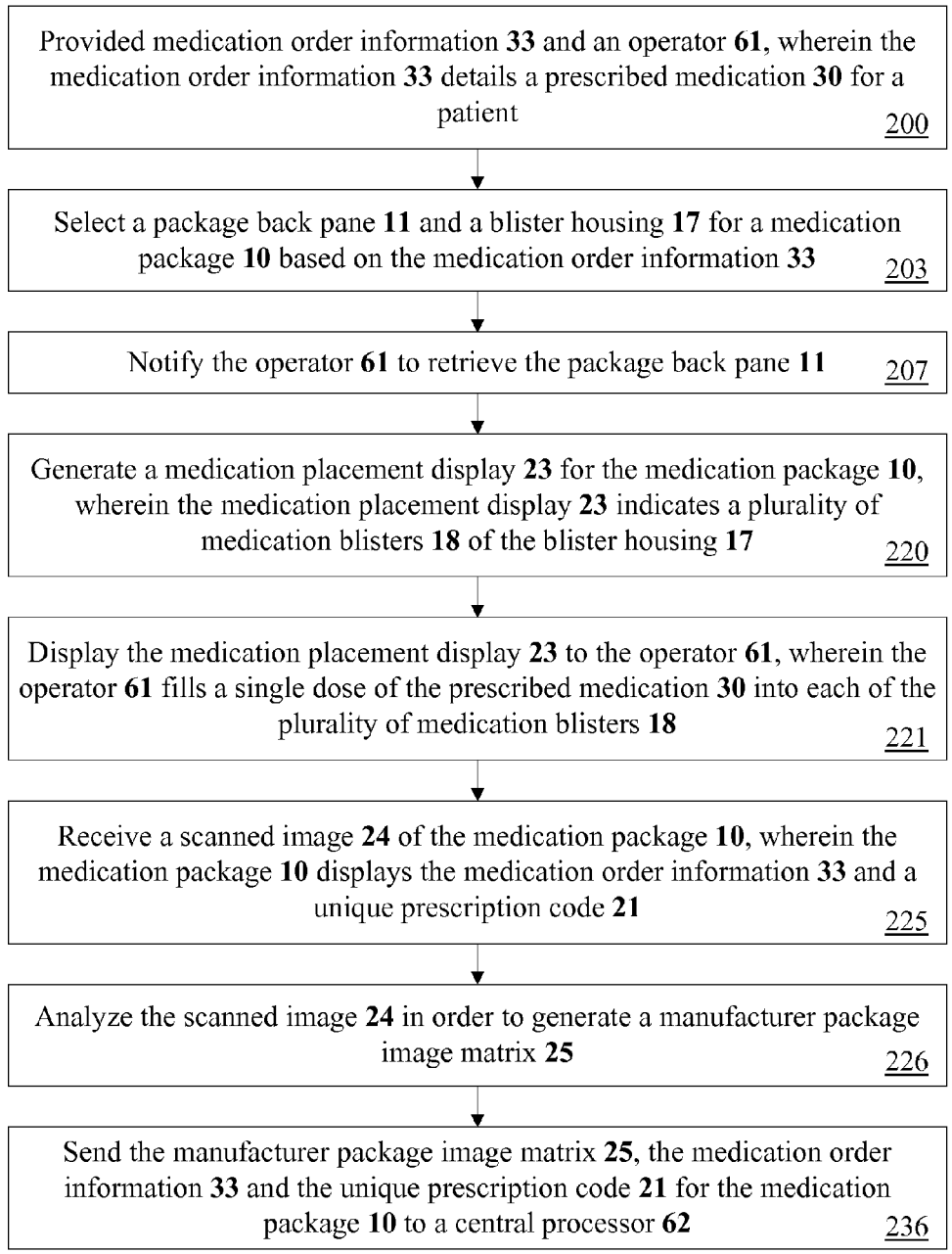
FIG. 4 is a flowchart of the steps taken by the order fulfillment processor in the manufacturing process.
Figure 5:
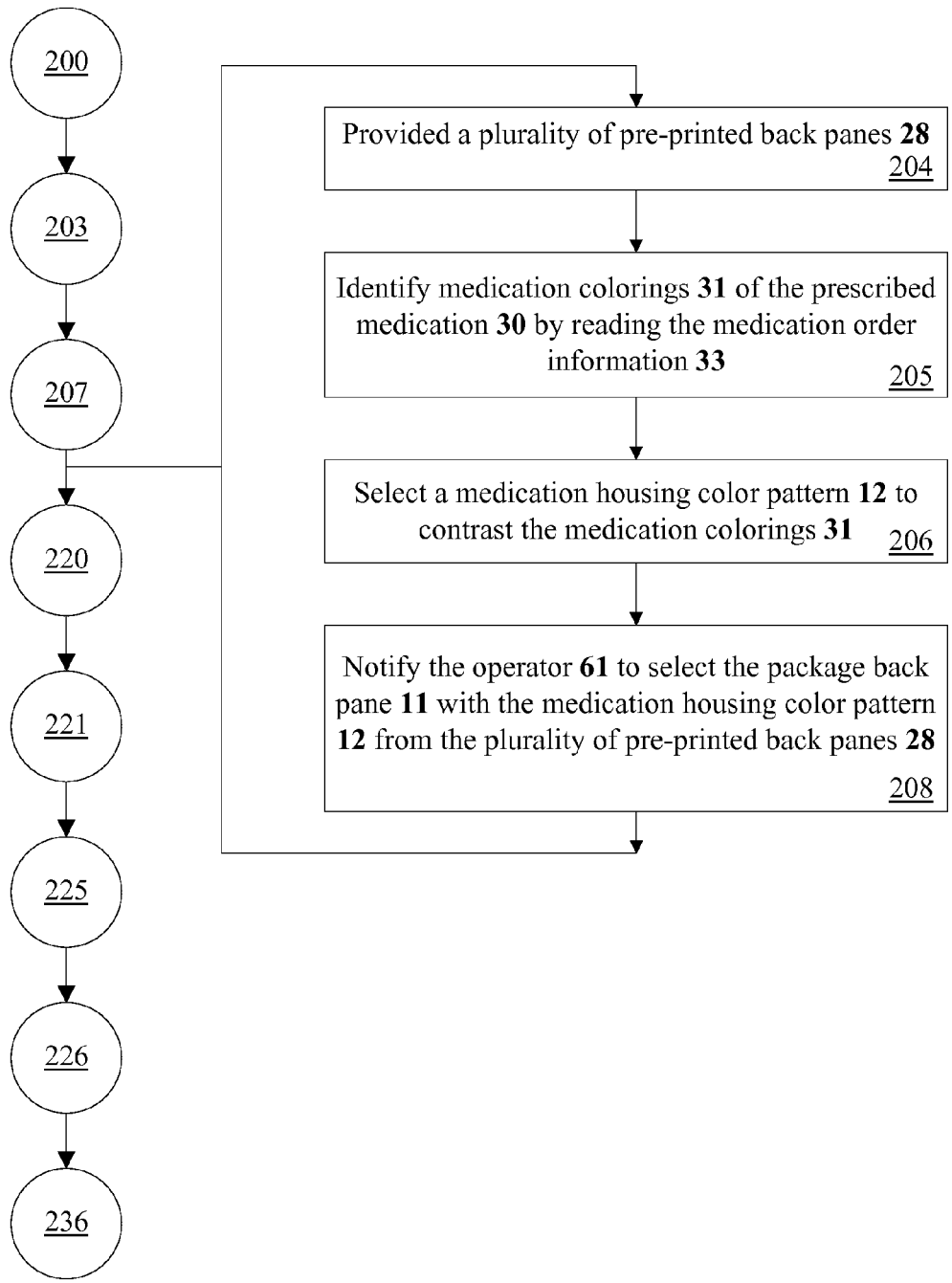
FIG. 5 is a flowchart detailing the additional steps for the order fulfillment processor to select a pre-printed package back pane in the manufacturing process.
Figure 6:
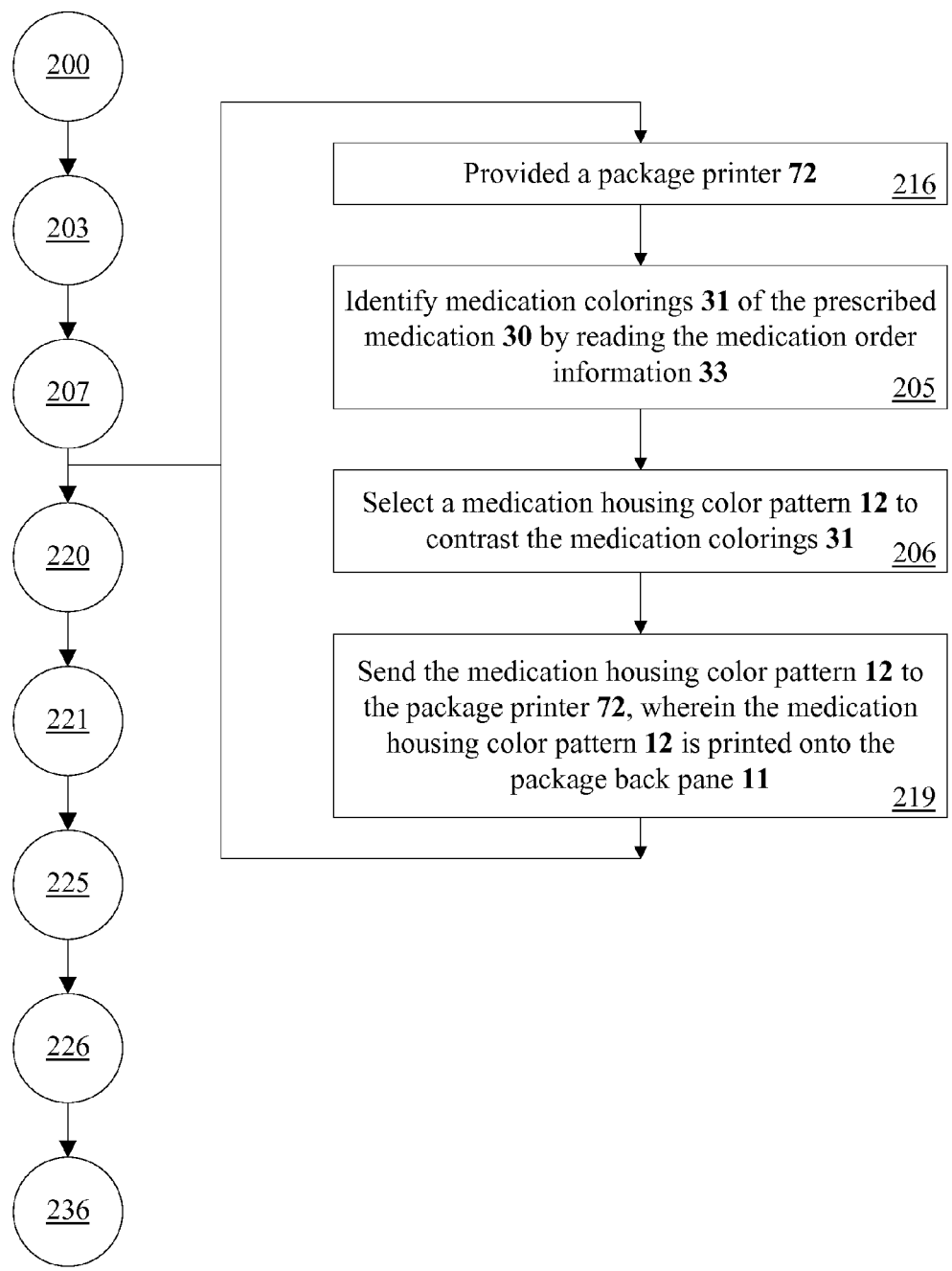
FIG. 6 is a flowchart detailing the additional steps for the order fulfillment processor to send the medication housing color pattern to the package printer if the package back pane is not pre-printed.

In reference to FIG. 4 and FIG. 11, provided an operator 61, the order fulfillment processor 60, and the medication order information 33 from a prescription order, wherein the medication order information 33 details a prescribed medication 30 for a patient, the order fulfillment process can be initiated [200], [201]. The order fulfillment processor 60 guides the operator 61 to select the prescribed medication 30 for the prescription order that has been sent to the order fulfillment processor 60 from either the third party information systems 68 or the central processor 62, via the communication network 66.

The operator 61 then scans or manually enters the NDC on a bulk package for the prescribed medication 30 into the order fulfillment processor 60 [202]. The order fulfillment processor 60 then selects the package back pane 11 and the blister housing 17 according to the physical and visual properties of the prescribed medication 30, the medication order information 33, and the physical and visual properties of the package back pane 11 [203].

The size and the number of doses of the prescribed medication 30 are determined by the medication order information 33, and are then used to determine the size and number of the plurality of medication blisters 18 of the blister housing 17 that are required. The size and number of the plurality of medication blisters 18 in turn determines the size of the package back pane 11. After the size of the package back pane 11 is decided, the medication colorings 31 of the prescribed medication 30 is identified by reading the medication order information 33 [205]. The medication colorings 31 is used to select the medication housing color pattern 12 for the medication package 10; the medication housing color pattern 12 contrasting the medication colorings 31 [206]. The package back pane 11 being the appropriate size and having the medication housing color pattern 12 as determined by the medication colorings 31 is then selected by the order fulfillment processor 60. Provided a plurality of pre-printed back panes 28 [204], after selecting the package back pane 11, the order fulfillment processor 60 notifies the operator 61 to retrieve the package back pane 11 [207] from the plurality of pre-printed back panes 28, wherein the package back pane 11 is pre-printed with the medication housing color pattern 12 [208].

Figure 12:
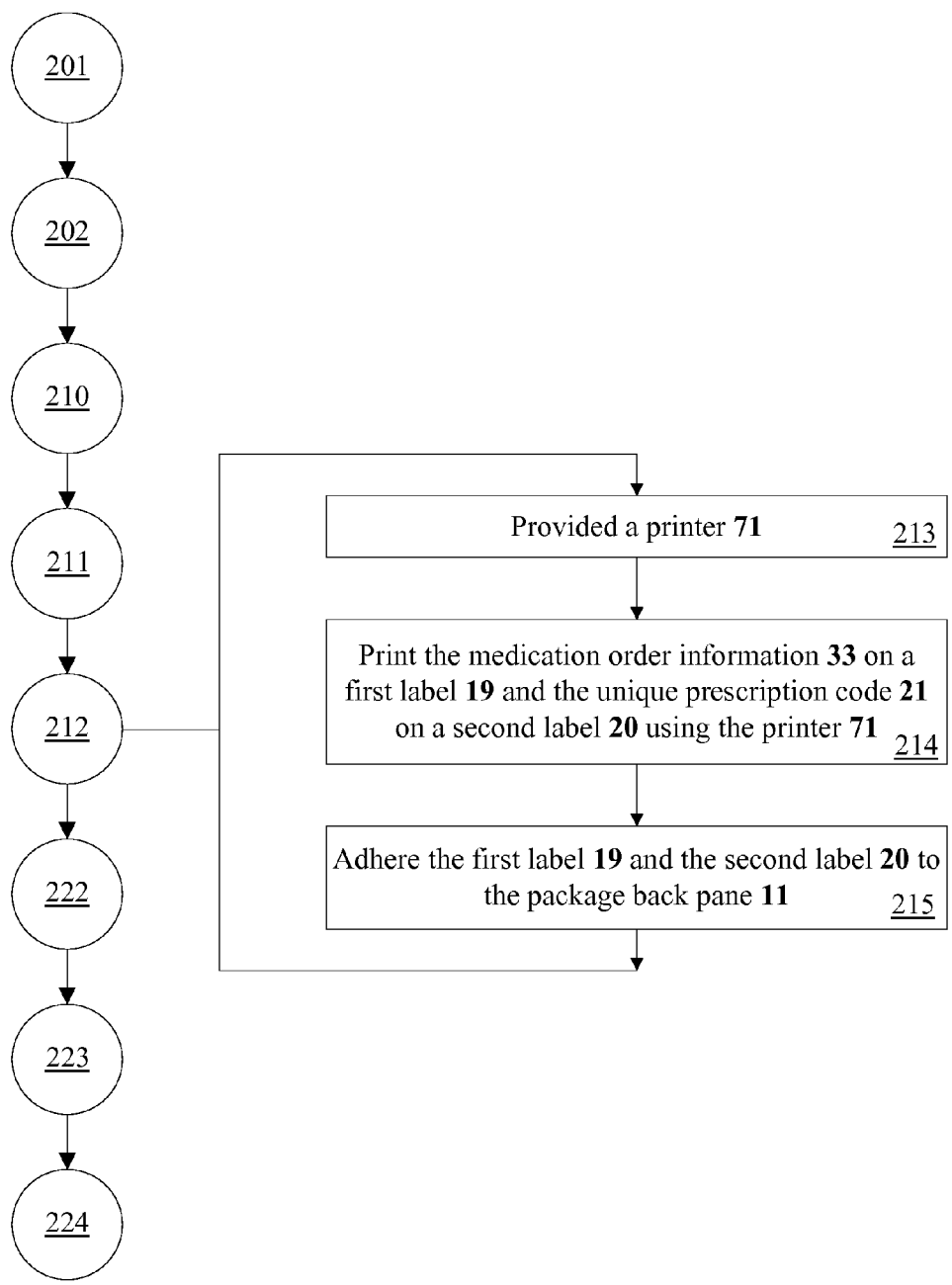
FIG. 12 is a flowchart detailing the steps of the operator printing the first label and the second label to be adhered to the package back pane.
Figure 13:
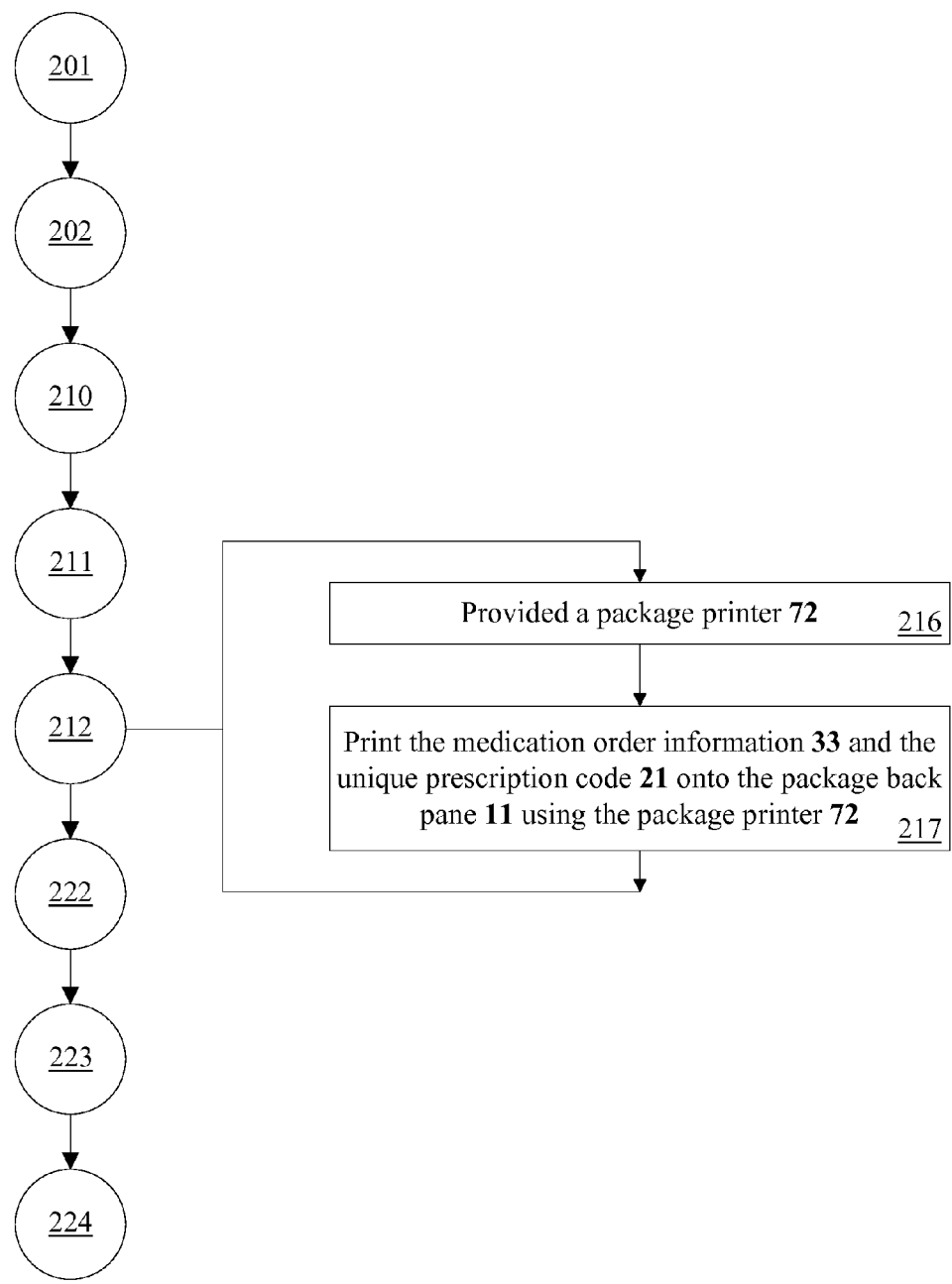
FIG. 13 is a flowchart detailing the steps of the operator printing the first label and the second label directly onto the package back pane.

In reference to FIG. 11-13, when the operator 61 has retrieved the package back pane 11 [210], the operator 61 scans the back pane code 22 using the code scanner 70 [211]. Information embedded in or referenced by the back pane code 22 is then validated by the order fulfillment processor 60 in order to ensure that the package back pane 11 selected by the operator 61 matches the package back pane 11 dictated by the order fulfillment processor 60. Once the package back pane 11 retrieved by the operator 61 has been validated, the operator 61 positions the medication order information and the unique prescription code on the package back pane [212]. Provided the printer 71 [213], the operator 61 utilizes the printer 71 to print the medication order information 33 on the first label 19 [214]. The first label 19 is then adhered to the package back pane 11 [215], adjacent to the medication housing color pattern 12, such that the first label 19 is visible to the patient or a caregiver. Alternatively, provided the package printer 72 [216], the medication order information 33 can be printed directly onto the package back pane 11 as the first label 19, using the package printer 72 [217].

Figure 14:
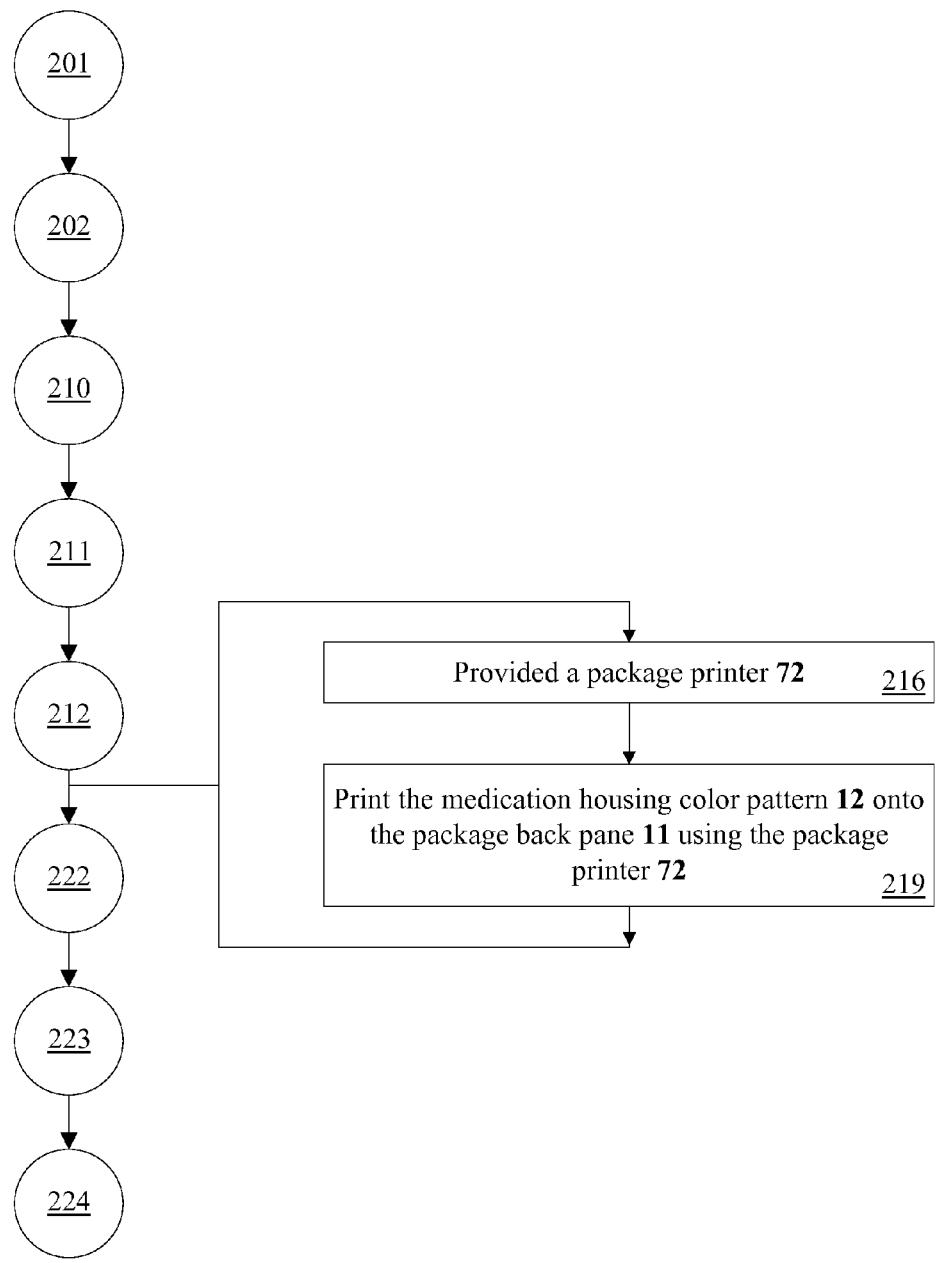
FIG. 14 is a flowchart detailing the steps of the operator printing the medication housing color pattern directly onto the package back pane.

In reference to FIG. 12-14, provided the printer 71 [213], the operator 61 prints the unique prescription code 21 onto the second label 20 using the printer 71 [214]. The second label 20 is then adhered to the package back pane 11 [215], adjacent to both the medication housing color pattern 12 and the first label 19. Similar to the medication order information 33, provided the package printer 72 [216], the unique prescription code 21 may be printed directly onto the package back pane 11 as the second label 20 using the package printer 72 [217]. The package printer 72 may also be used to print the medication housing color pattern 12 onto the package back pane 11 [219], if the package back pane 11 is not selected from the plurality of pre-printed back panes 28 or the plurality of pre-printed back panes 28 is not provided.

In reference to FIG. 4 and FIG. 11, after the package back pane 11 has been validated, the order fulfillment processor 60 generates a medication placement display 23 for the medication package 10 [220]; particularly the blister housing 17. The medication placement display 23 is then displayed to the operator 61, wherein the medication placement display 23 indicates the plurality of medication blisters 18 of the blister housing 17 into which the prescribed medication 30 is to be placed [221]. Correct placement may be indicated on the order fulfillment processor 60 by highlighting, circling or otherwise marking the plurality of medication blisters 18 in the medication placement display 23.

The operator 61 then fills the plurality of medication blisters 18, while referencing the medication placement display 23 in order to ensure that the prescribed medication 30 is properly distributed. A single dose 32 of the prescribed medication 30 is filled into each of the plurality of medication blisters 18 by the operator 61. Once the prescribed medication 30 has been correctly dispersed among the plurality of medication blisters 18 [222], the operator 61 seals the blister housing 17 with the package back pane 11 in order to form the medication package 10 [223]; wherein each of the plurality of medication blisters 18 is sealed around one of the plurality of medication housing indicators 13. Any known packaging method for blister packs may be used to connect the package back pane 11 to the blister housing 17.

The medication placement display 23 is of particular benefit when the medication package 10 contains multiple types of medication, as different medications may be housed together or separately depending on the prescribed administration of the medications. For example, a patient is prescribed amoxicillin and oxybutynin. If the prescribed administration is the same for each type of medication (e.g. both are taken once a day at night), then a single dose 32 of amoxicillin and a single dose 32 of oxybutynin are filled into each of the plurality of medication blisters 18. As another example, a patient is prescribed amoxicillin and oxybutynin, but the prescribed administration for each is different (e.g. both are taken once a day, but one is administered at night and the other in the morning). A single dose 32 of amoxicillin may then be filled in each of the plurality of medication blisters 18 forming a first row or column of the blister housing 17, while a single dose 32 of oxbutynin is filled in each of the plurality of medication blisters 17 forming a second row or column of the blister housing 17.

Figure 7:
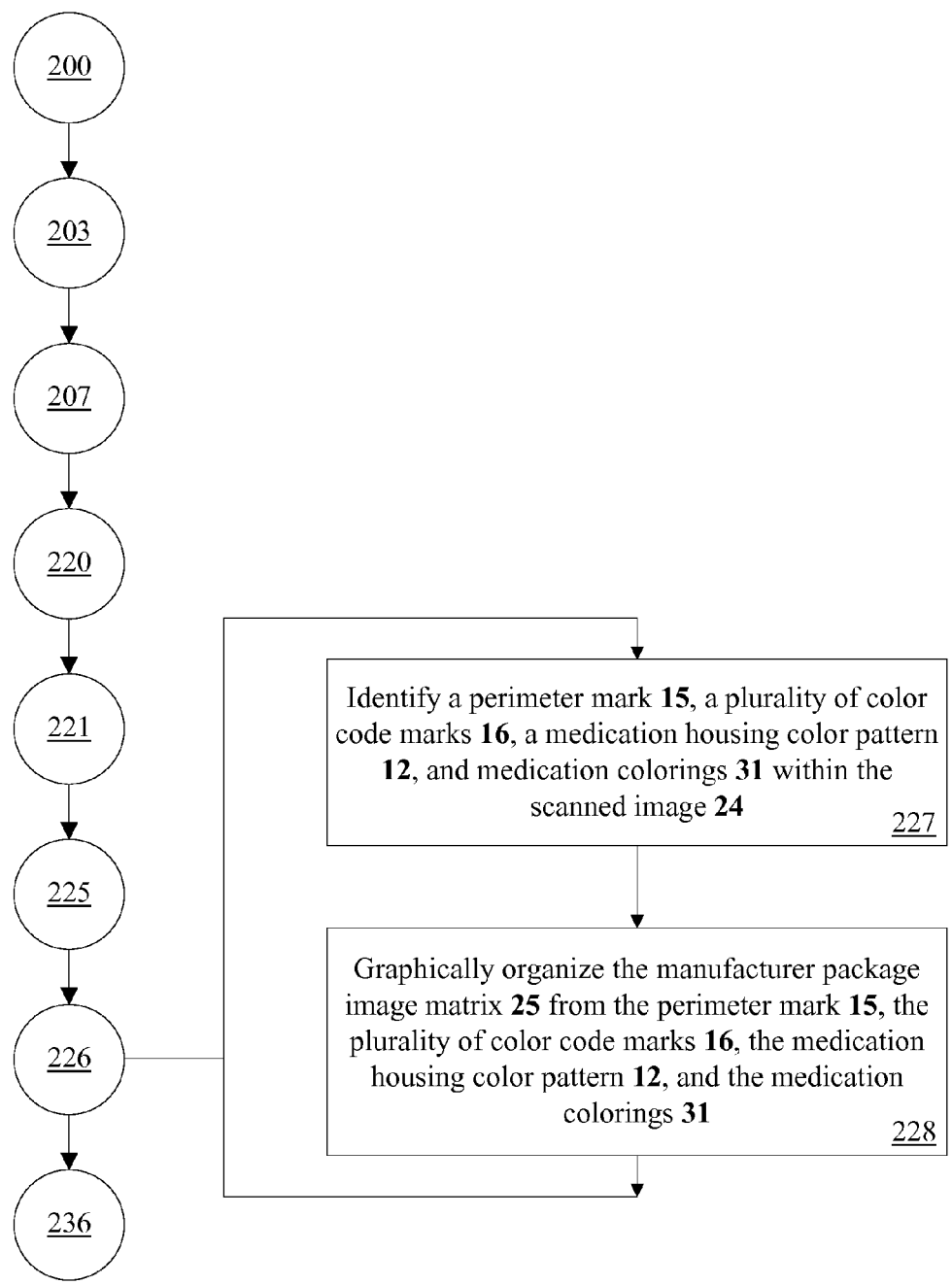
FIG. 7 is a flowchart detailing the steps for the order fulfillment processor to generate the manufacturer package image matrix.

In reference to FIG. 4 and FIG. 7, upon assembly of the medication package 10, the operator 61 scans the medication package 10 using the digital imaging device 73 [224]. The digital imaging device 73 can be a camera, scanner, or any other device capable of capturing a still image. A scanned image 24 of the medication package 10 is then sent from the digital imaging device 73 and received by the order fulfillment processor 60 [225]. The scanned image 24 of the medication package 10 is then saved on the order fulfillment processor 60. By analyzing the scanned image 24, the order fulfillment processor 60 then generates a manufacturer package image matrix 25 from visual characteristics of the medication package 10 [226]; specifically by identifying the medication housing color pattern 12, the medication colorings 31, the plurality of color code marks 16, and the perimeter mark 15 within the scanned image [227]. The order fulfillment processor 60 uses the medication housing color pattern 12, the medication colorings 31, the plurality of color code marks 16, and the perimeter mark 15 to graphically organize the manufacturer package image matrix 25 from the scanned image 24 [228].

Figure 8:
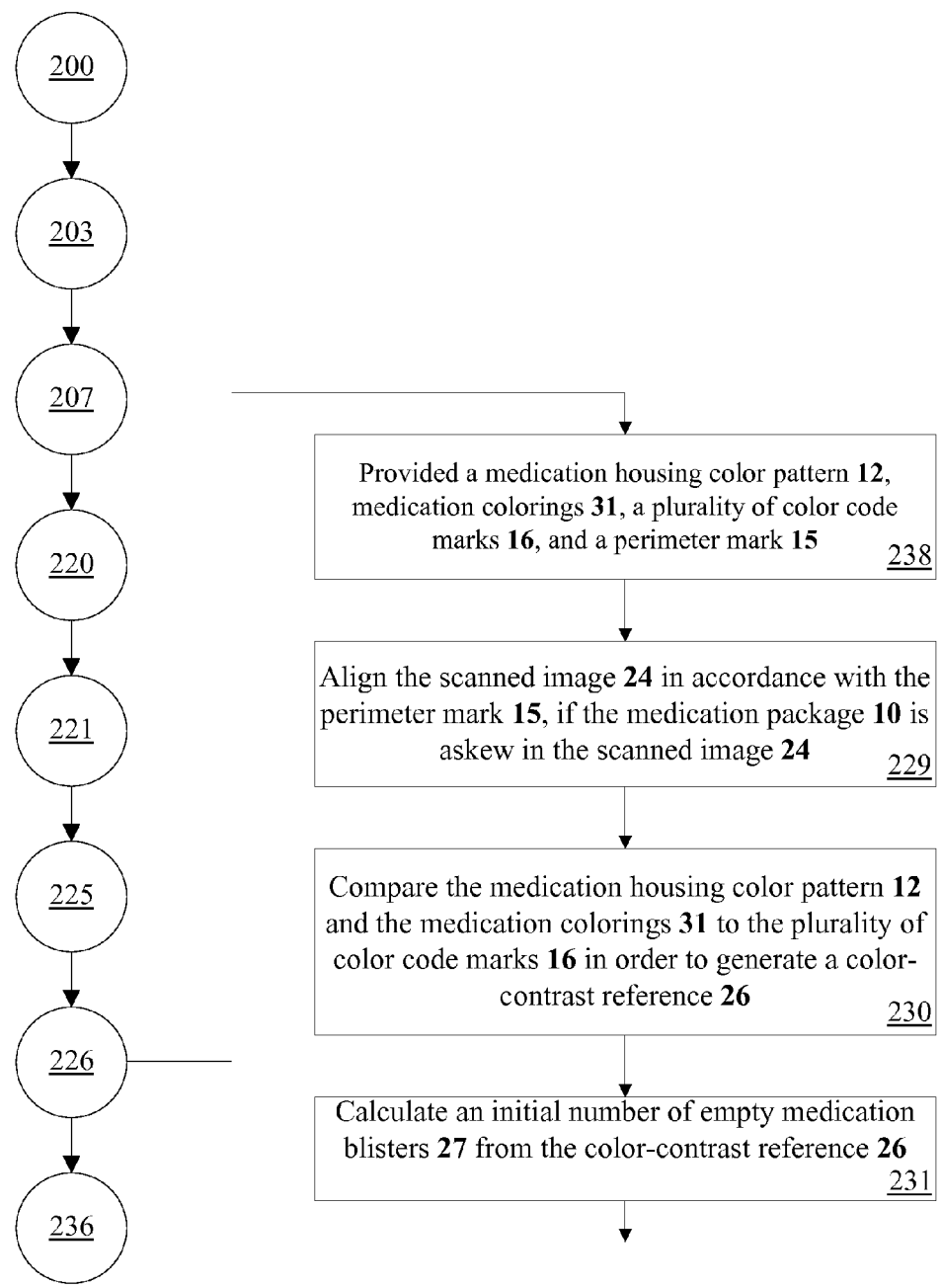
FIG. 8 is a flowchart detailing the steps for calculating an initial number of empty medication blisters provided the information obtained in the steps of FIG. 7.
Figure 9:
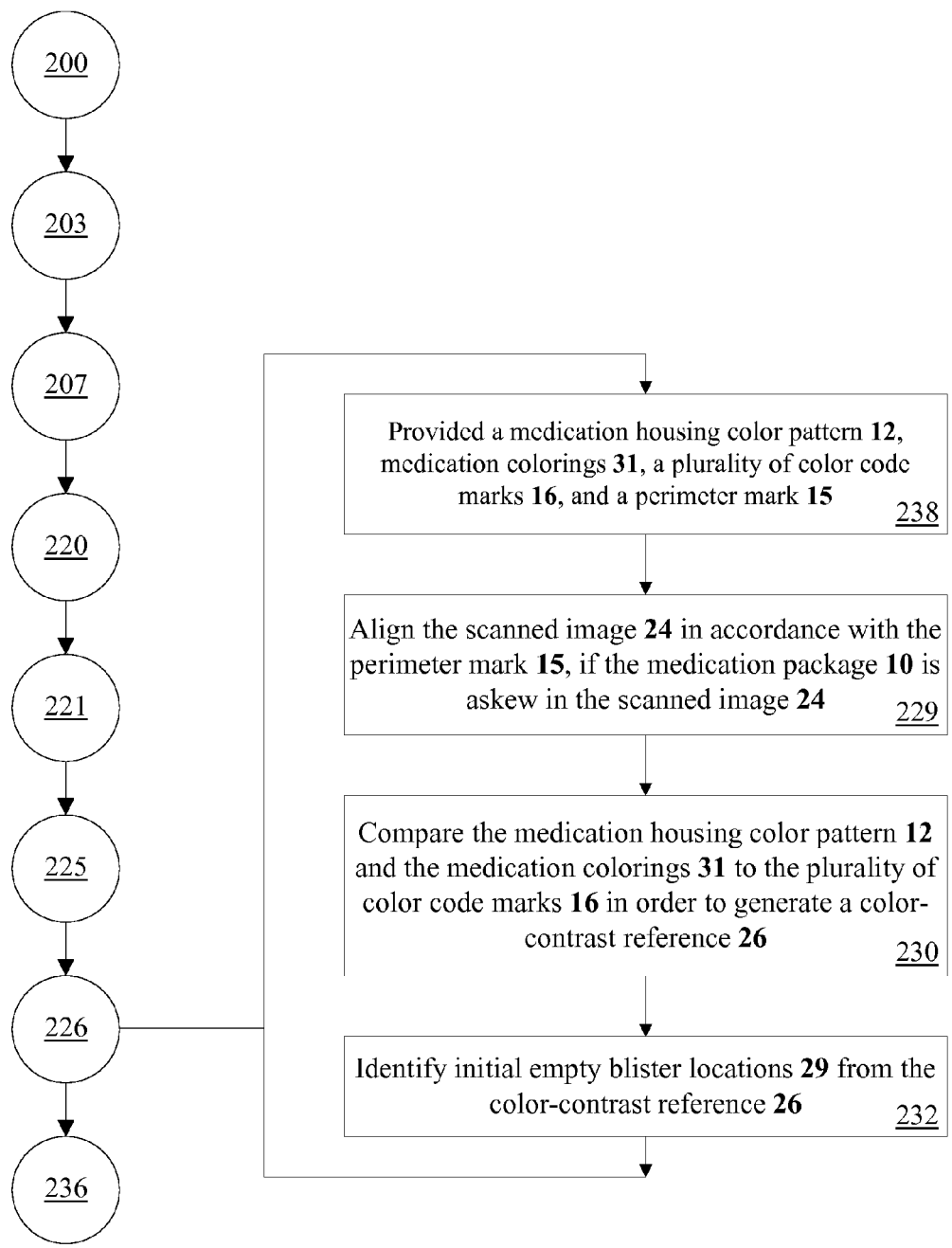
FIG. 9 is a flowchart detailing the steps for identifying initial empty blister locations provided the information obtained in the steps of FIG. 7.

In reference to FIG. 8 and FIG. 9, provided the medication housing color pattern 12, the medication colorings 31, the perimeter mark 15, and the plurality of color code marks 16 [238]; the perimeter mark 15 is used to align the scanned image 24, if the medication package 10 is askew in the scanned image 24 [229]. Additionally, the perimeter mark 15 may be used to crop the scanned image 24. Once the scanned image 24 is aligned properly, the medication housing color pattern 12 and the medication colorings 31 are compared to the plurality of color code marks 16 in order to generate a color-contrast reference 26 [230]. The color-contrast reference 26 is then used to calculate an initial number of empty medication blisters 27 by measuring the light contrast about each of the plurality of medication housing indicators 13 [231].

There is a predetermined contrast ratio for each of the plurality of medication housing indicators 13 that depends on the size of the prescribed medication 30. A current contrast ratio for each of the plurality of medication housing indicators 13 is determined and compared to the predetermined contrast ratio in order to determine if each of the plurality of medication blisters 18 is or is not filled with the prescribed medication 30. For example, if the predetermined contrast ratio is twenty five percent, then the single dose 32 of the prescribed medication 30 in each of the plurality of medication blisters 18 should obstruct twenty five percent of each of the plurality of medication housing indicators 13 associated with each of the plurality of medication blisters amoxicillin and oxybutynin that should be filled. If the current contrast ratio does not match the predetermined contrast ratio, then it can be determined that the given medication blister is not filled with the prescribed medication 30.

The initial number of empty medication blisters 27 should be zero, any other value indicates that the medication package 10 has been tampered with or incorrectly assembled. The color-contrast reference 26 is also used to identify initial empty blister locations 29 of the plurality of medication blisters 18 [232]. This is carried out to ensure that each of the plurality of the medication blisters 18 is properly filled at the time of manufacture. Each of the plurality of medication blisters 18 is then identified in the manufacturer package image matrix 25 with a mark to indicate whether or not the prescribed medication 30 within has been administered. The same process can also be used to determine an initial number of filled medication pockets and initial filled blister locations if desired. If the initial number of filled medication pockets is used, then the initial number of filled medication pockets should match the number of the plurality of medication blisters.

Figure 10:
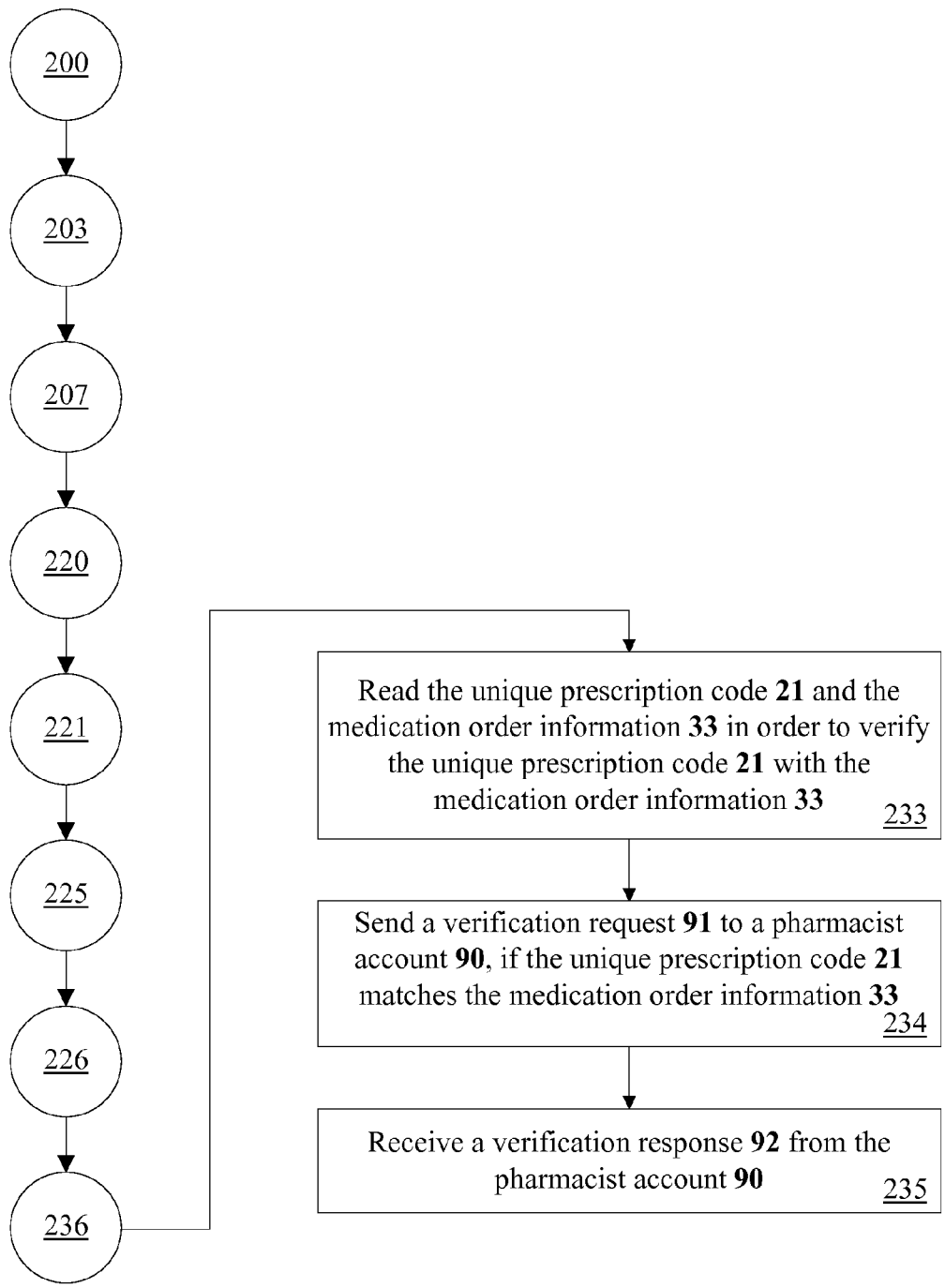
FIG. 10 is a flowchart detailing the steps of verifying the medication package once the medication package has been assembled.

In reference to FIG. 10, upon receiving the scanned image 24, the order fulfillment processor 60 also analyzes the scanned image 24 and automatically verifies the medication package 10. The medication package 10 is verified by comparing data from the unique prescription code 21 to the medication order information 33 in order to verify the unique prescription code 21 with the medication order information 33 [233]. If the data from the unique prescription code 21 matches the data from the medication order information 33, then the medication package 10 is verified and the order fulfillment processor 60 sends a verification request 91 to a pharmacist account 90 [234]. The order fulfillment processor 60 then receives a verification response 92 from the pharmacist account 90 as to whether or not the medication package 10 was authenticated [235]. The pharmacist account 90 provides a user interface between a pharmacist and the order fulfillment processor 60, and can be initiated on any electronic device capable of connecting to the communication network 66. Upon successful verification by the pharmacist, the order fulfillment processor 60 sends the scanned image 24, the unique prescription code 21 and associated data, the medication order information 33, and any other prescription data to the central processor 62 [236]. The second scanned image, the unique prescription code 21 and associated data, the medication order information 33, and any other prescription data is then stored in a medication database 63 on the central processor 62. The medication package 10 can then be distributed to the patient or patient's health care provider.

Figure 15:
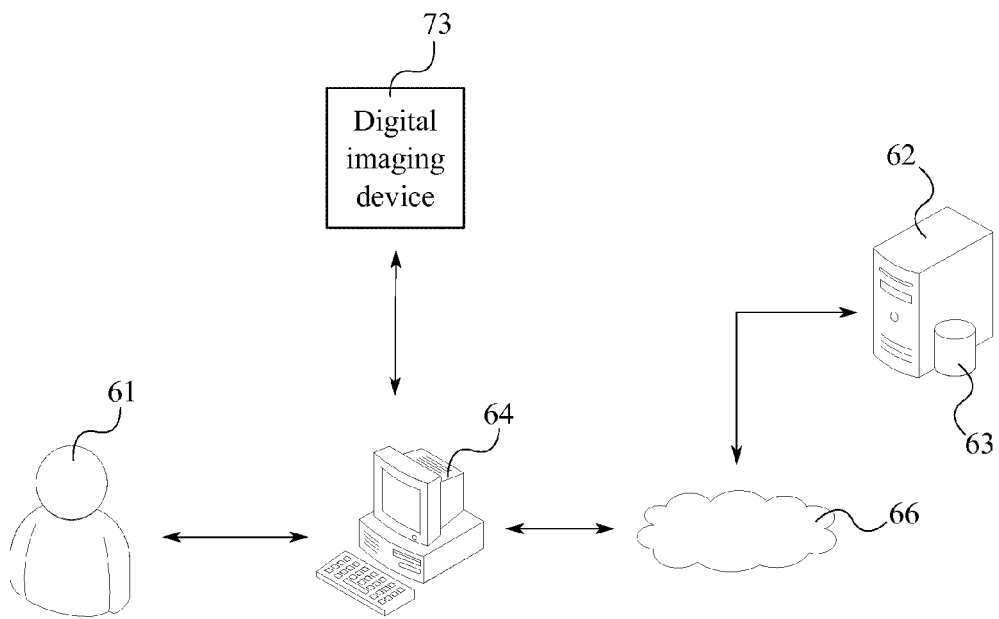
FIG. 15 is a diagram depicting the device and administrator interactions for the scheduling process and the administration process.
Figure 16:
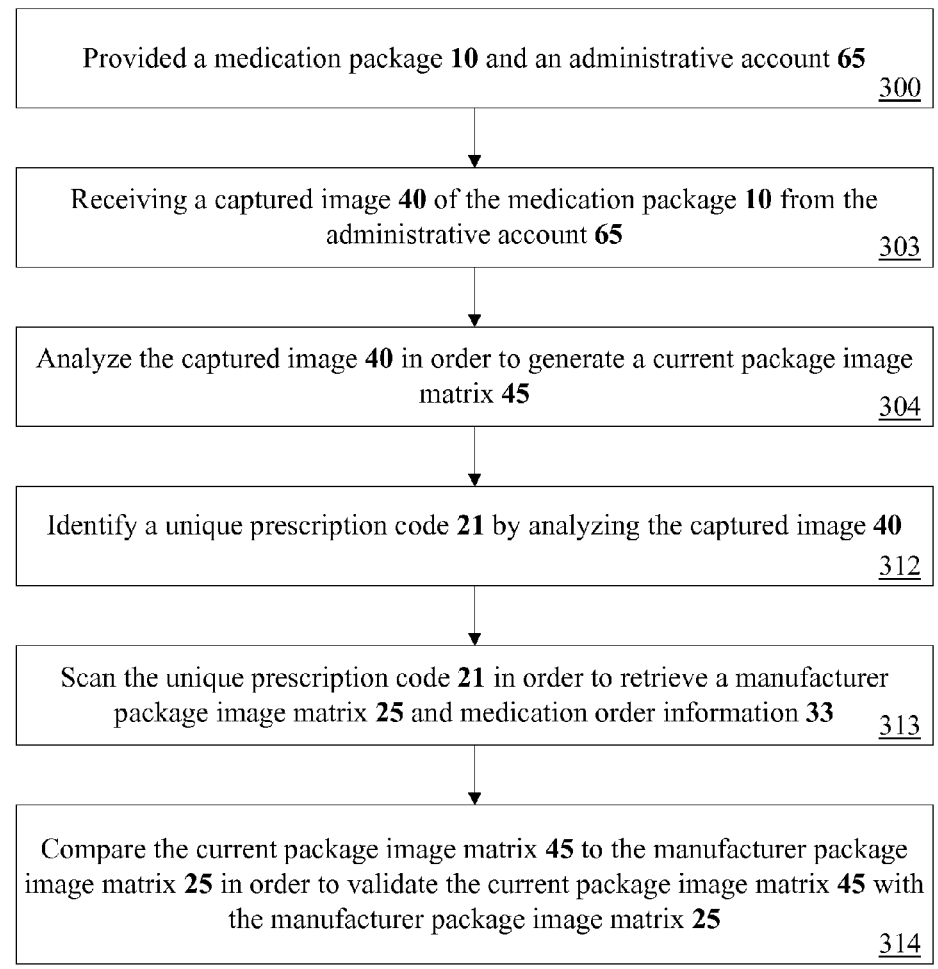
FIG. 16 is a flowchart of the steps taken by the administration processor in the scheduling process and the administration process.

In reference to FIG. 15, the medication scheduling process includes the use of the central processor 62 in communication with an administrative processor 64 via the communication network 66. The administrative processor 64 can be any type of electronic device with a digital imaging device 73 and the ability to connect to the communication network 66. An administrative account 65 provides a user interface on the administrative processor 64. The central processor 62 receives the manufacturer package image matrix 25 and the medication order information 33 from the order fulfillment processor 60 and stores the manufacturer package image matrix 25 and the medication order information 33 in the medication database 63. In reference to FIG. 16, provided the medication package 10 and the administrative account 65 [300], a patient or caregiver receives the medication package 10 and then uses the administrative processor 64 to obtain a captured image 40 of the medication package 10. The captured image 40 is sent to the central processor 62 via the communication network 66, while a copy of the captured image 40 is saved locally on the administrative processor 64 [303]. Upon receiving the captured image 40, the central processor 62 analyzes the captured image 40 in order to generate a current package image matrix 45 [304].

Figure 17:
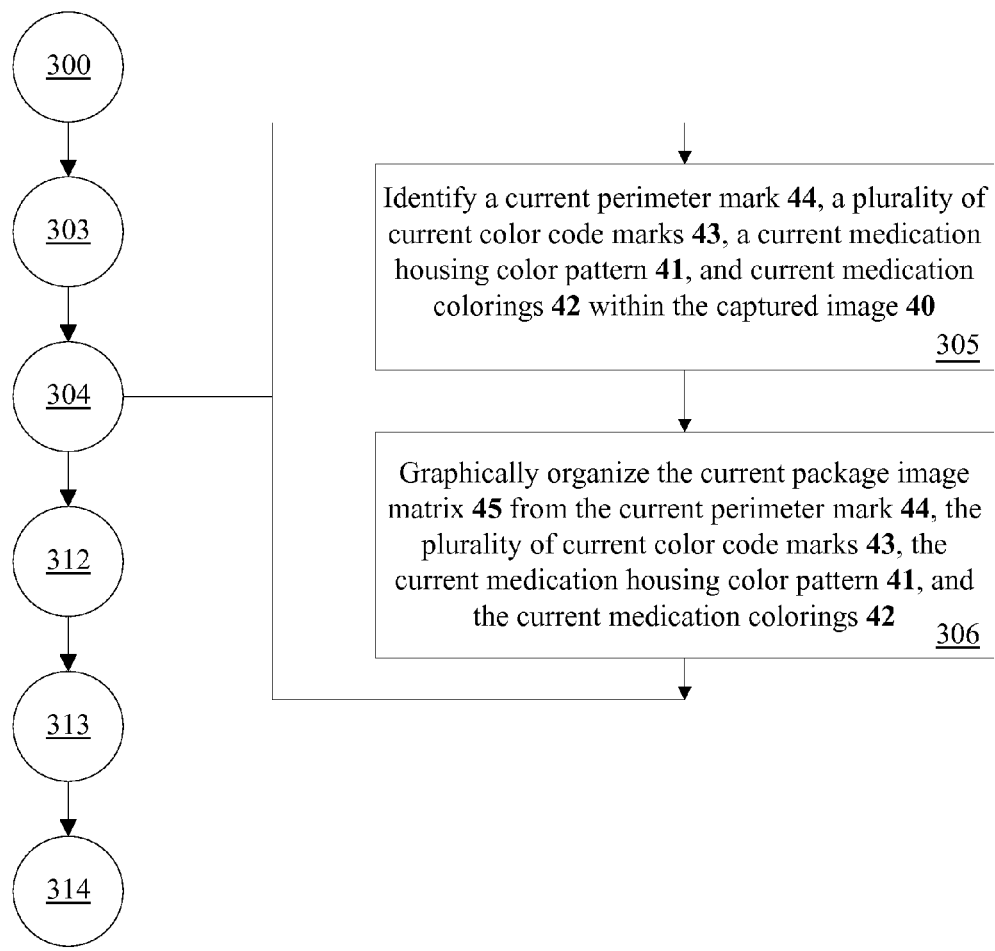
FIG. 17 is a flowchart detailing the steps for the administration processor to generate the current package image matrix.

In reference to FIG. 17, by analyzing the captured image 40, the administrative processor 64 generates the current package image matrix 45 from visual characteristics of the medication package 10; specifically by identifying a current medication housing color pattern 41, current medication colorings 42, a plurality of current color code marks 43, and a current perimeter mark 44 from the captured image 40 [305]. The administrative processor 64 uses the current medication housing color pattern 41, the current medication colorings 42, the plurality of current color code marks 43, and the current perimeter mark 44 to graphically organize the current package image matrix 45 from the captured image 40 [306]. In another embodiment of the present invention, the current package image matrix 45 may be generated by the central processor 62.

Figure 18:
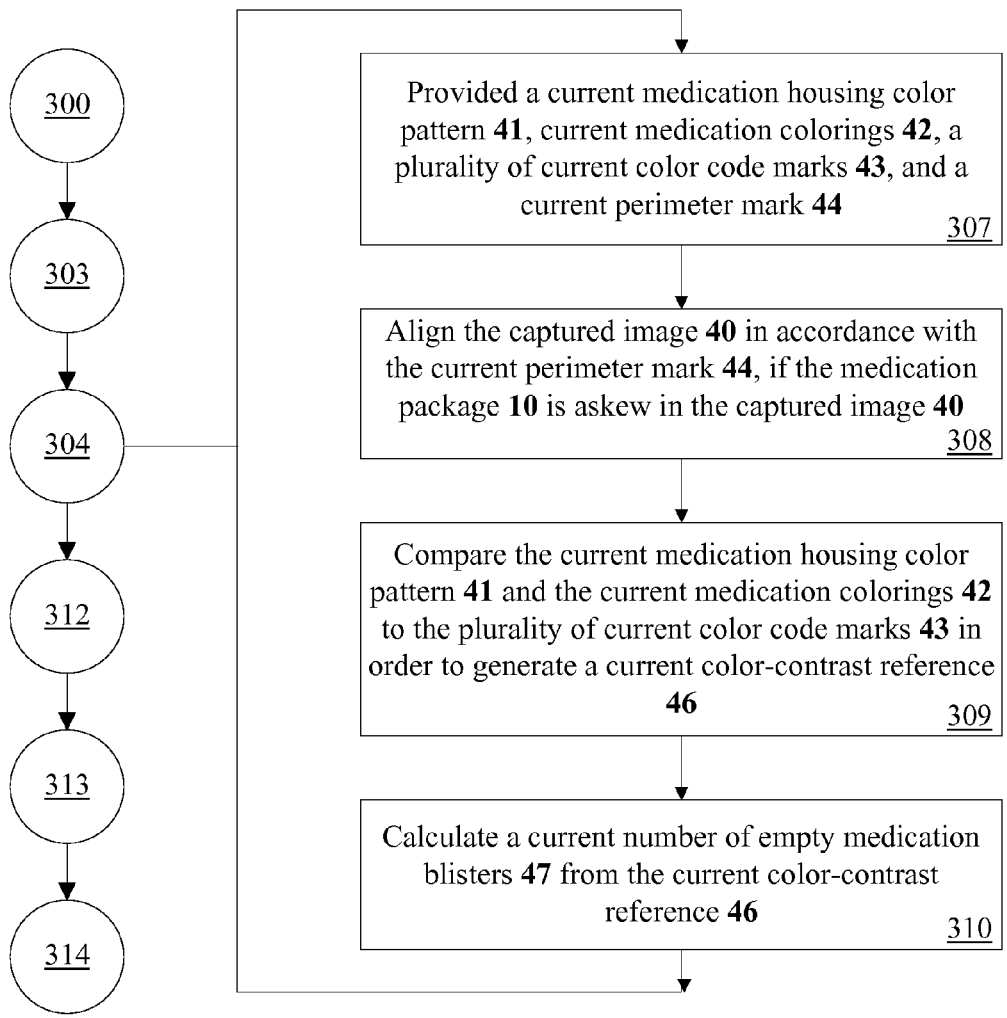
FIG. 18 is a flowchart detailing the steps for calculating an current number of empty medication blisters provided the information obtained in the steps of FIG. 17.
Figure 19:
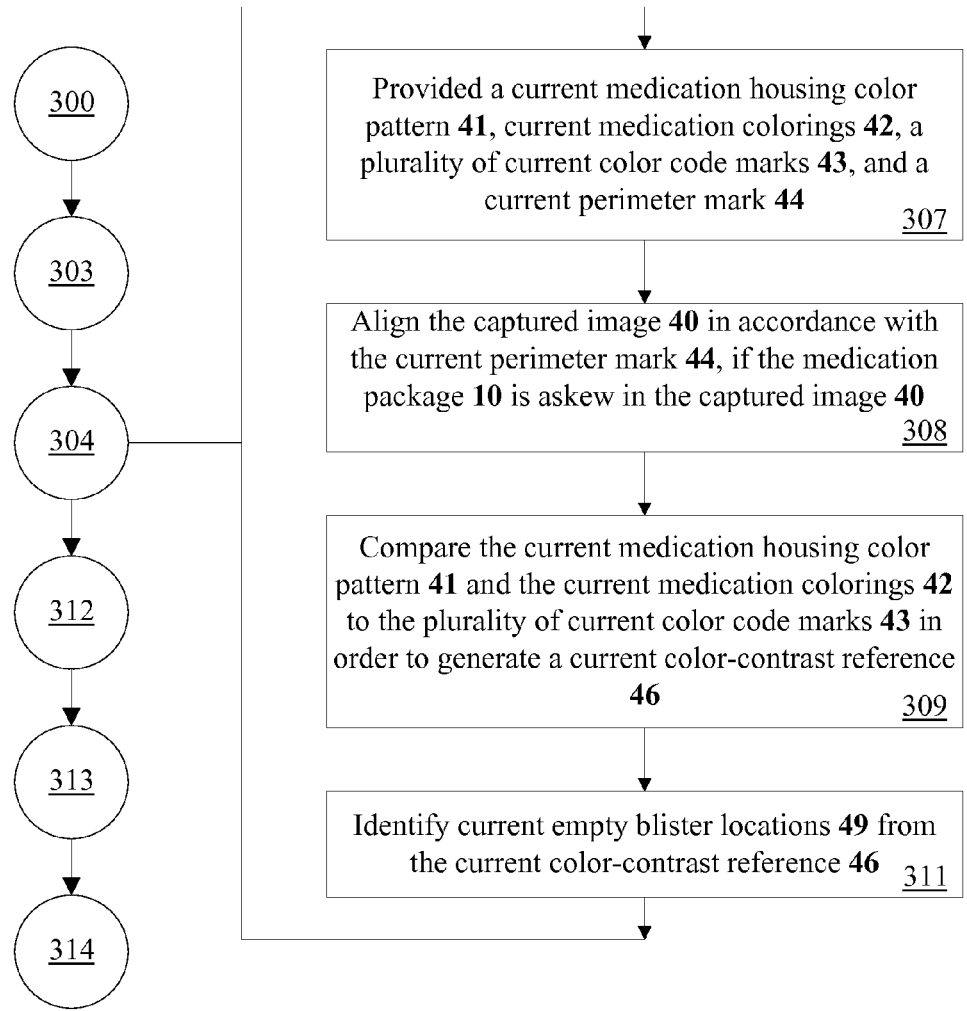
FIG. 19 is a flowchart detailing the steps for identifying current empty blister locations provided the information obtained in the steps of FIG. 17.

In reference to FIG. 18-19, provided the current medication housing color pattern 41, the current medication colorings 42, the plurality of current color code marks 43, and the current perimeter mark 44 [307]; the current perimeter mark 44 is used to align the captured image 40, if the medication package 10 is askew in the captured image 40 [308]. Additionally, the current perimeter mark 44 may be used to crop the captured image 40. Once the captured image 40 is aligned properly, the current medication housing color pattern 41 and the current medication colorings 42 are compared to the plurality of current color code marks 43 in order to generate a current color-contrast reference 46 [309]. The current color-contrast reference 46 is then used to calculate a current number of empty medication blisters 47 by measuring the light contrast about each of the plurality of medication housing indicators 13 [310]. The current color-contrast reference 46 is also used to identify current empty blister locations 49 of the plurality of medication blisters 18 in order to determine if a dose of the prescribed medication has been improperly administered [311]. Each of the plurality of medication blisters 18 is then identified in the current package image matrix 45 with a mark to indicate whether or not the prescribed medication 30 within has been administered. The same process can also be used to determine a current number of filled medication pockets and current filled blister locations if desired.

In reference to FIG. 16, when the administrative processor 64, or the central processor 62, receives the captured image 40, the administrative processor 64, or the central processor 62, also extracts the unique prescription code 21 by analyzing the captured image 40 [312]. The unique prescription code 21 is then scanned by the administrative processor 64, or the central processor 62, in order to retrieve the medication order information 33 and the manufacturer package image matrix 25 [313]. If information is embedded in the unique prescription code 21, then the medication order information 33 and the manufacturer package image matrix 25 are retrieved and displayed on the administrative processor 64. The administrative processor 64 then compares the current package image matrix 45 to the manufacturer package image matrix 25 in order to validate the current package image matrix 45 with the manufacturer package image matrix 25 [314]. Step [314] is to ensure that the medication package 10 is not defective, has not been tampered with, etc.

If information is referenced by the unique prescription code 21, then the central processor 62 searches through the medication database 63 in order to locate the medication order information 33 and the manufacturer package image matrix 25 associated with the unique prescription code 21. Once the reference of the unique prescription code 21 is located in the medication database 63, the central processor 62 retrieves the medication order information 33 and the manufacturer package image matrix 25 associated with the unique prescription code 21. The central processor 62 then compares the current package image matrix 45 to the manufacturer package image matrix 25 in order to validate the current package image matrix 45 with the manufacturer package image matrix 25 [314].

Figure 20:
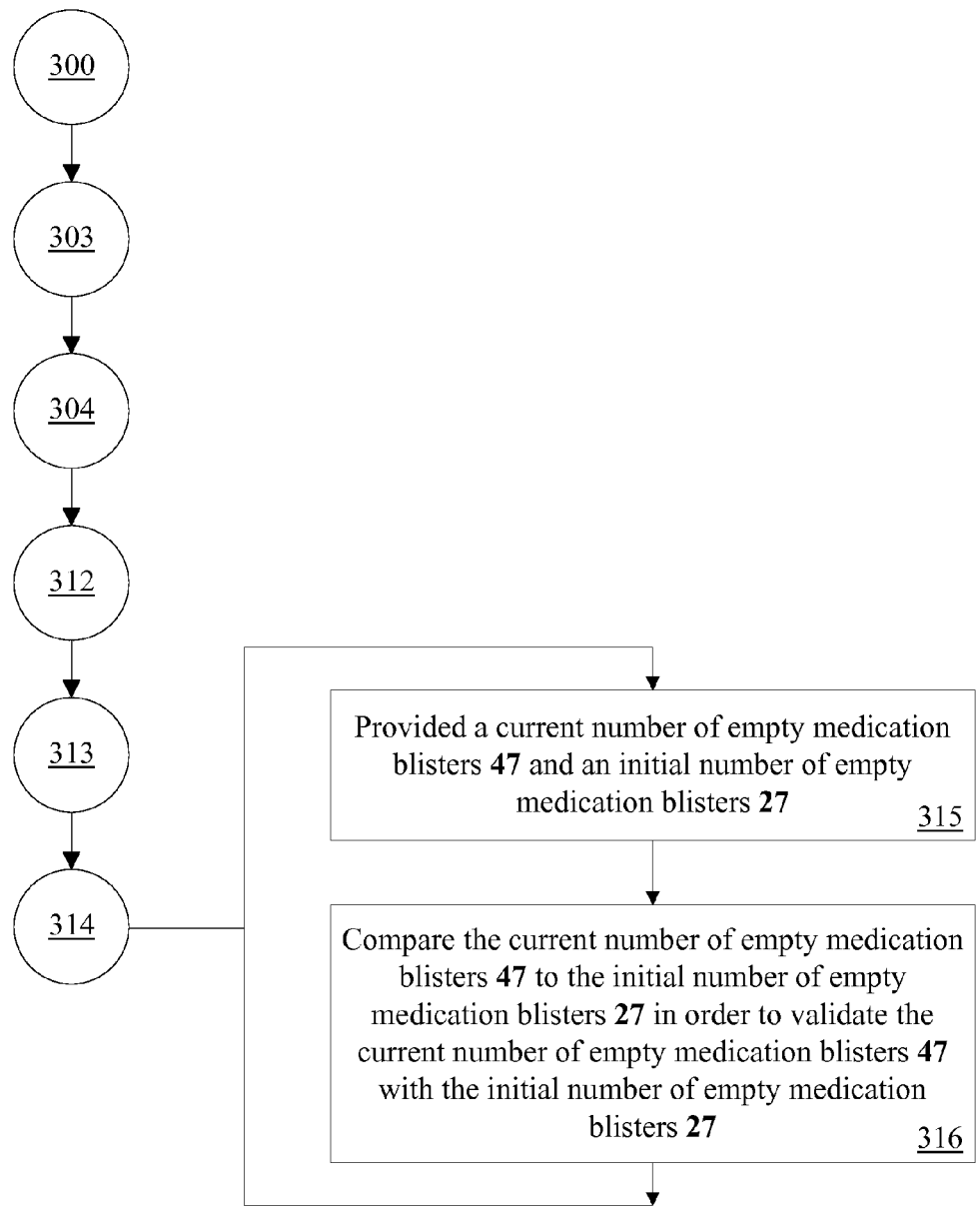
FIG. 20 is a flowchart detailing the steps of verifying the medication package by comparing the initial number of empty medication blisters and the current number of empty medication blisters.
Figure 21:
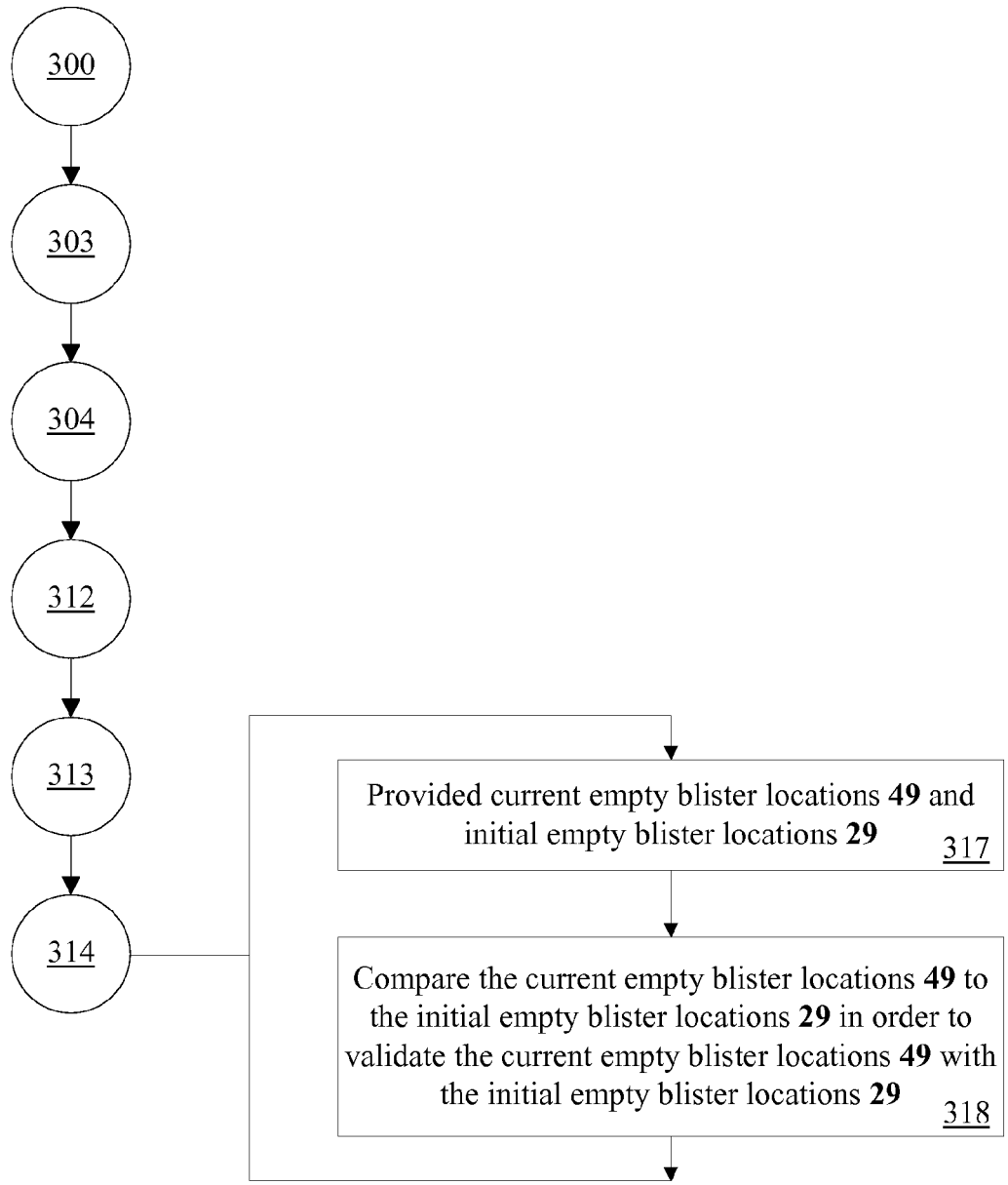
FIG. 21 is a flowchart detailing the steps of verifying the medication package by comparing the initial empty blister locations and the current empty blister locations.

In reference to FIG. 20-21, provided the current number of empty medication blisters 47 and the initial number of empty medication blisters 27 [315] and provided the current empty blister locations 49 and the initial empty blister locations 29 [317]; the current package image matrix 45 is validated with the manufacturer package image matrix 25 by comparing the initial number of empty medication blisters 27 to the current number of empty medication blisters 47 and by comparing the initial empty blister locations 29 to the current empty blister locations 49. The initial number of empty medication blisters 27 is compared to the current number of empty medication blisters 47 in order to validate the current number of empty medication blisters 47 with the initial number of empty medication blisters 27 [316]. The current number of empty medication blisters 47 must match the initial number of empty medication blisters 27 in order to validate the current number of empty medication blisters 47. Similarly, the initial empty blister locations 29 is compared to the current empty blister locations 49 in order to validate the current empty blister locations 49 with the initial empty blister locations 29 [318]. The current empty blister locations 49 must match the initial empty blister locations 29 in order to validate the current number of empty medication blisters 47.

Figure 22:
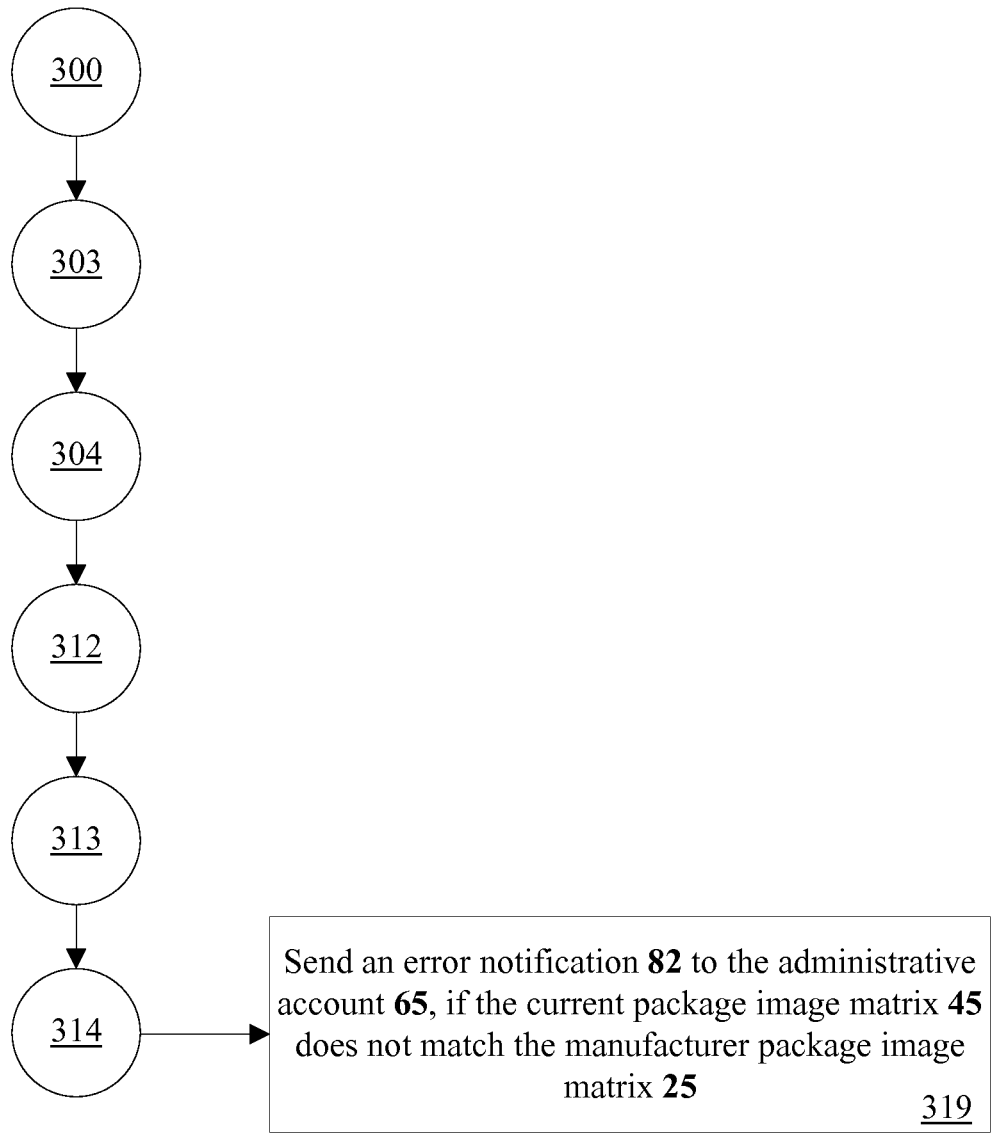
FIG. 22 is a flowchart showing the response for a medication package that is not validated.

In reference to FIG. 22, if the current package image matrix 45 does not match the manufacturer package image matrix 25, then an error notification 82 is sent from the administrative processor 64, or the central processor 62, to the administrative account 65 [319]. The error notification 82 can be an audible and/or visual indicator. The caregiver can then follow a facility's internal process for damaged or tampered medication packages, or the patient can follow instructions on the medication package 10 concerning how to handle damaged or tampered medication packages [320].

Figure 23:
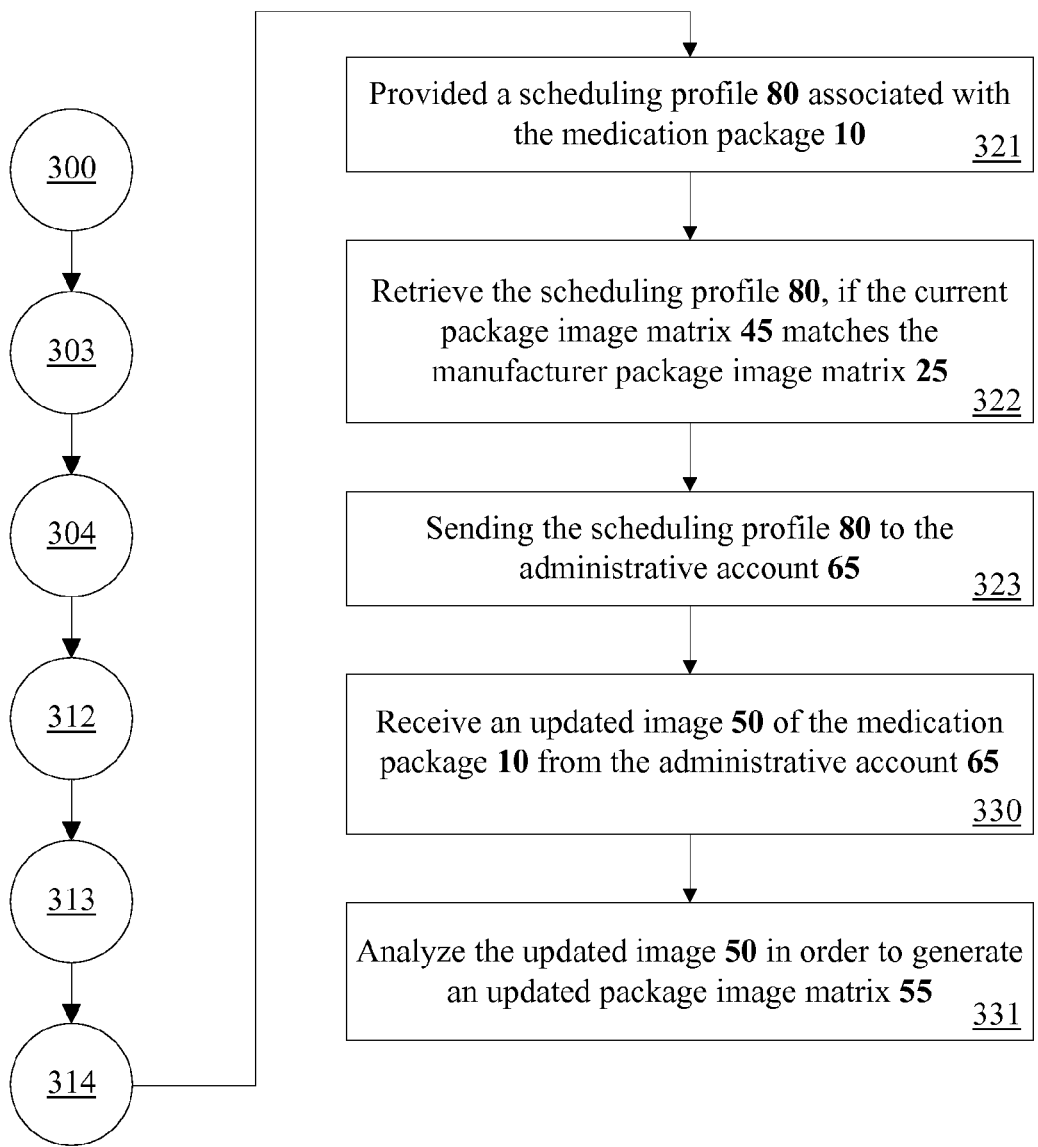
FIG. 23 is a flowchart detailing the steps for retrieving a scheduling profile if the medication package is validated.

In reference to FIG. 23, if the current package image matrix 45 matches the manufacturer package image matrix 25, then the central processor 62 will search for a scheduling profile 80 for administering the prescribed medication 30. Provided the scheduling profile 80 associated with the medication package 10 [321], the scheduling profile 80 is retrieved from the unique prescription code 21. If the scheduling profile 80 for the patient is found to be embedded in the unique prescription code 21, then the administrative processor 64 retrieves the scheduling profile 80 [322] and sends the scheduling profile 80 to the administrative account 65 to be observed by the patient or caregiver [323]. The scheduling profile 80 is also stored locally on the administrative processor 64 in order to notify the patient or caregiver of future administration of the prescribed drug 30.

Alternatively, if the unique prescription code 21 references information in the medication database 63, then the central processor 62 finds the scheduling profile 80 in the medication database 63. The scheduling profile 80 is then retrieved from the medication database 63 by the central processor 62 [322]. Upon retrieving the scheduling profile 80, the central processor 62 sends the scheduling profile 80 to the administrative account 65 on the administrative processor 64 [323]. The scheduling profile 80 is then stored locally on the administrative processor 64.

Figure 24:
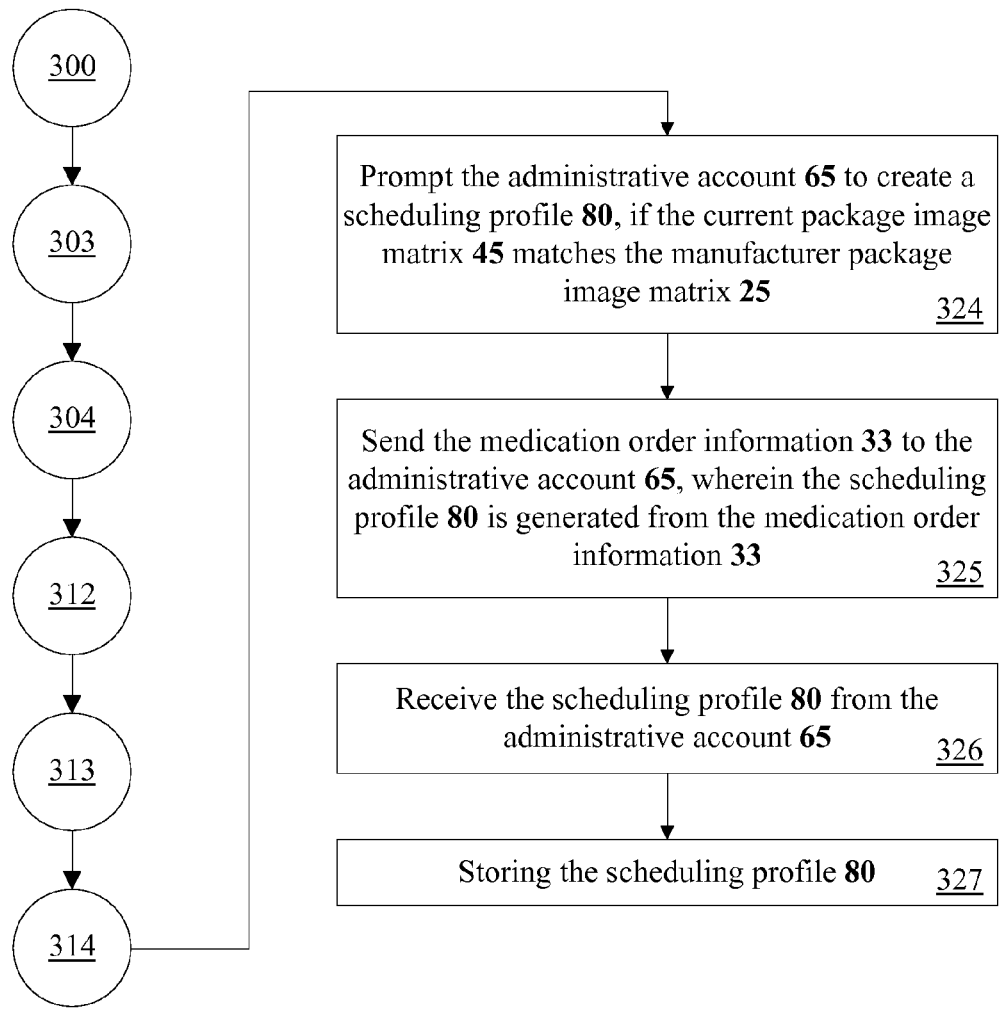
FIG. 24 is a flowchart detailing the steps for creating the scheduling profile if the scheduling profile is not available.

In reference to FIG. 24, if the scheduling profile 80 is not found to be embedded in the unique prescription code 21 or is not found in the medication database 63, then the administrative processor 64 prompts the administrative account 65 to create the scheduling profile 80 [324]. If the medication order information 33 is embedded in the unique prescription code 21, then the medication order information 33 is retrieved by the administrative processor and sent to the administrative account 65 [325]. The medication order information 33 is automatically organized into the scheduling profile 80 by the administrative processor 64 before being sent to the administrative account 65. The patient or caregiver can then verify information in the scheduling profile 80 through the administrative account 65. It is also possible for the patient or caregiver to manually edit the scheduling profile 80 through the administrative account 65.

Alternatively, the medication order information 33 can be retrieved from the medication database 63 by the central processor 62. Upon retrieving the medication order information 33, the central processor 62 sends the medication order information 33 to the administrative account 65 via the administrative processor 64 [325]. Again, the medication order information 33 is automatically organized into the scheduling profile 80 by the administrative processor 64 before being sent to the administrative account 65. The patient or caregiver can then verify the scheduling profile 80 and manually edit the scheduling profile 80 if necessary.

In further reference to FIG. 24, once the scheduling profile 80 is created, the scheduling profile 80 is received by the administrative processor 64 from the administrative account 65 [326]. The scheduling profile 80 can also be received by the central processor 62 from the administrative account 65 via the administrative processor 64. Upon receiving the scheduling profile 80 from the administrative account 65, the administrative processor 64 stores the scheduling profile locally 80, while the central processor 62 stores the scheduling profile 80 in the medication database 63 [327].

In reference to FIG. 15, the administration process provides a system for guiding, monitoring and keeping records of medication administration compliance and includes the use of the central processor 62, the communication network 66, and the administrative processor 64. Once the scheduling profile 80 has been created, the administrative processor 64 will notify the patient or caregiver when the next dose of the prescribed medication 30 should be administered from the medication package 10. Once the patient or caregiver acknowledges the notification, a last saved image of the medication package 10 is displayed on the administrative processor 64 through the administrative account 65, if the last saved image is available. In reference to FIG. 16, for the first administration, the patient or caregiver collects the medication package 10 and scans the medication package 10 using the digital imaging device 73 of the administrative processor 64 in order to obtain a captured image 40 of the medication package 10. When the administrative processor 64, or the central processor 62, receives the captured image 40 [303], the administrative processor 64, or the central processor 62, analyzes the captured image 40 in order to generate a current package image matrix 45 [304] and identify the unique prescription code 21 of the medication package 10 [312]. The unique prescription code 21 is then scanned by the administrative processor 64, or the central processor 62, in order to retrieve the medication order information 33 and the manufacturer package image matrix 25 [313]. The scheduling profile 80 is then verified with the medication order information 33 to ensure the prescribed medication 30 should be administered at the given time.

If an incorrect medication package 10 is scanned (e.g. it is not the correct time to take the selected medication, or it is the wrong medication), then the administrative processor 64 notifies the patient or caregiver. When the medication package 10 has been selected, scanned and verified, the administrative processor 64, or the central processor, 62, compares the current package image matrix 45 to the manufacturer package image matrix 25 [314].

When a missing dose is detected, the administrative processor 64 notifies the patient or caregiver. If the missing dose was administered but not recorded, then the patient or caregiver can enter the time and date of administration. If the missing dose was not administered, then the missing dose is recorded on the administrative processor 64 and the central processor 62. When no missing dose is detected, the administrative processor 64 instructs the patient or caregiver to administer the prescribed medication 30. The administrative processor 64 indicates a specific medication pocket from the plurality of medication blisters 18 from which the prescribed medication 30 should be taken. The specific medication pocket from which to take the prescribed medication 30 can be indicated using any number of methods such as highlighting or circling the specific medication pocket in the captured image 40 or current package image matrix 45.

In reference to FIG. 23, once the prescribed medication 30 has been administered from the specific medication pocket, the patient or caregiver again scans the medication package 10 in order to obtain an updated image 50 of the medication package 10. The updated image 50 is then stored locally on the administrative processor 64 and sent from the administrative processor 64 to the central processor 62. Upon receiving the updated image 50 of the medication package 10 [330], the administrative processor 64 or the central processor 62 analyzes the updated image 50 in order to generate an updated package image matrix 55 [331]. The updated package image matrix 55 is then stored locally on the administrative processor 64 or remotely in the medication database 63 on the central processor 62. The updated package image matrix 55 is then used as a point of reference the next time the prescribed medication 30 is administered. The updated package image matrix 55 is created in the same manner as the current package image matrix 45 and the manufacturer package image matrix 25. If an incorrect dose was administered (i.e. the prescribed medication 30 was not administered from the specific medication pocket, then the administrative processor 64 will notify the patient or caregiver. The next medication administration is calculated using the scheduling profile 80 and is stored on the administrative processor 64 or the central processor 62.

Although the invention has been explained in relation to its preferred embodiment, it is to be understood that many other possible modifications and variations can be made without departing from the spirit and scope of the invention as hereinafter claimed.

What is claimed is:

1. A medication package comprises:
 a package back pane;
 a medication housing color pattern;
 a plurality of reference marks;

a blister housing;

the blister housing comprises a plurality of medication blisters;

the medication housing color pattern and the plurality of reference marks being positioned on the package back pane;

the plurality of reference marks being positioned around the medication housing color pattern;

the blister housing being connected to the package back pane;

the plurality of medication blisters being positioned adjacent to the medication housing color pattern; and the blister housing being transparent, wherein the medication housing color pattern is visible through the plurality of medication blisters.

2. The medication package as claimed in claim 1 comprises:

the plurality of reference marking comprises a perimeter mark and a plurality of color code marks; and the perimeter mark and the plurality of color code marks being positioned around the plurality of medication package housings.

3. The medication package as claimed in claim 1 comprises:

a unique prescription code; and the unique prescription code being positioned on the package back pane adjacent to the medication housing color pattern.

4. The medication package as claimed in claim 1 comprises:

a back pane code; and the back pane code being positioned on the package back pane adjacent to the medication housing color pattern.

* * * * *